United States Patent [19]
Koch et al.

[11] Patent Number: 5,843,404
[45] Date of Patent: *Dec. 1, 1998

[54] DETECTION OF HYPOXIA

[75] Inventors: Cameron J. Koch, Phila., Pa.; Edith M. Lord, Rochester, N.Y.

[73] Assignees: Trustees of the University of Pennsylvania, Philadelphia, Pa.; Trustees of the University of Rochester, Rochester, N.Y.

[ * ] Notice: The term of this patent shall not extend beyond the expiration date of Pat. No. 5,540,918.

[21] Appl. No.: 598,752

[22] Filed: Feb. 8, 1996

Related U.S. Application Data

[60] Division of Ser. No. 286,065, Aug. 4, 1994, Pat. No. 5,540,908, which is a continuation-in-part of Ser. No. 978,918, Nov. 19, 1992, abandoned.

[51] Int. Cl.$^6$ ........................ A61K 51/10; A61K 101/02; A61K 31/415; G01N 33/531

[52] U.S. Cl. .......................... 424/934; 424/149; 424/189; 424/937; 424/174.1; 424/184.1; 530/387.1; 530/391.1

[58] Field of Search ................................. 424/1.49, 1.89, 424/9.34, 9.37, 175.1, 181.1; 422/61; 530/362, 404, 405, 406

[56] References Cited

U.S. PATENT DOCUMENTS

| | | | |
|---|---|---|---|
| 3,679,698 | 7/1972 | Beaman et al. | 548/327.5 |
| 4,241,060 | 12/1980 | Smithen | 374/212 |
| 4,371,540 | 2/1983 | Lee et al. | 424/273 R |
| 4,797,397 | 1/1989 | Suto et al. | 514/212 |
| 4,816,401 | 3/1989 | Taupier et al. | 435/240.31 |
| 4,927,941 | 5/1990 | Kagiya et al. | 548/264.8 |
| 4,977,273 | 12/1990 | Kagiya et al. | 548/339 |
| 5,030,036 | 7/1991 | Huff et al. | 405/266 |
| 5,086,068 | 2/1992 | Raleigh et al. | 514/398 |
| 5,304,654 | 4/1994 | Kagiya et al. | 548/327.5 |

OTHER PUBLICATIONS

Kennedy et al., *Biochem. Pharm.*, 1980, 29, 1–8.
Moulder et al., *Int. J. Radioat. Oncol. Biol. Phys.* 1984, 10, 695–712.
Adams, *Cancer*, 1981, 48, 696–707.
Chapman et al., "The Fraction of Hypoxic Clonogenic Cells . . . ", *Biol. Bases Clin. Imp. Tum. Rad.*, G.H. Fletcher, C. Nevil, & H.R. Withers, (eds.), 1983, 61–73.
Urtasun et al., "A novel technique for measuring human tissue $pO_2$ at the cellular level", *Br. J. Cancer*, 1986, 54, 453–457.
Koch et al., *Int. J. Radiation Oncology Biol. Phys.*, 1984, 10, 1327.
Chapman et al., *Int. J. Radiat. Oncol. Biol. Phys.*, 1989, 16, 911–917.
Taylor et al., *Cancer Res.*, 1978, 38, 2745–2752.
Varghese et al., *Cancer Res.*, 1980, 40, 2165–2169.
Franko et al., *Cancer Res.* ,1987, 47, 5367–5376.
Rasey et al., *Radiat. Res.*, 1987, 111, 292–304.
Raleigh et al., *Int. J. Radiat. Oncol. Biol. Phys.*, 1984, 10, 1337–1340.
Raleigh et al., *Br. J. Cancer*, 1987, 56, 395.
Parliament et al., *Br. J. Cancer*, 1992, 65, 90–95.
Koch, "Selective Activation of Drugs by Redox Processes, Plenum Press", 1990, 237–247.
Lord, et al., "Detection of Hypoxic Cells by Monoclonal Antibody . . . Adducts", *Cancer Res.*, 1993, 53, 5721–5726.
Koch et al., "Radiolytic Reduction of Protien and Nonprotien Disulfides in the Presence of Formate: A Chain Reaction", *Arch. Biochem. Biophs.*, 1991, 287, 75–84.
Franko et al., Recent Results in Cancer Res. in 94 Culture of Cellular Spheroids 62, 1984, 95, 162–167.
Kohler et al., *Nature*, 1975, 256, 495.
Knauf et al., *Cancer Immunol. Immunotherapy*, 1986, 21, 217–225.
Harwell et al., *J. Immunol. Methods*, 1984, 66, 59–67.
Koch, *Radiat. Res.*, 1984, 97, 434–442.
Raleigh et al., "Importance of Thiols In The Reductive Binding of 2–Nitroimidazoles to Macromolecules", *Biochem. Pharmacol.*, 1990, 40, 2457–2464.
Beaman et al., Chemical Abstract 71(5): 22065t, 1967.
Grunberg et al., Chemical Abstract 70(3):10175v, 1968.
Heindel et al, *J. Pharm. Sci.*, 1987, 76(5), 384–386.
Evidence that hypoxia markers detect oxygen gardients in liver: pimonidazole and retrograde perfusion of rat liver, GE Arteel, RG Thurman, JM Yates and JA Raleigh, *British Journal Of Cancer*, 1995, 72(4),889–95.

*Primary Examiner*—Ponnathamurthy Achutamurth
*Attorney, Agent, or Firm*—Woodcock Washburn Kurtz Mackiewicz & Norris LLP

[57] ABSTRACT

Novel nitroaromatic compounds and immunogenic conjugates comprising a novel nitroaromatic compound and a carrier protein are disclosed. The invention further presents monoclonal antibodies highly specific for the claimed nitroaromatic compounds, the compounds' protein conjugates, the compounds' reductive byproducts, and adducts formed between the compounds and mammalian hypoxic cell tissue proteins. The invention is further directed to methods for detecting tissue hypoxia using immunohistological techniques, non-invasive nuclear medicinal methods, or nuclear magnetic resonance. Diagnostic kits useful in practicing the methods of claimed invention are also provided.

15 Claims, 15 Drawing Sheets

DETECTION OF HYPOXIA

RELATED APPLICATIONS

This is a division of application Ser. No. 08/286,065, filed Aug. 4, 1994, now U.S. Pat. No. 5,540,908, which is a continuation-in-part of Ser. No. 07/978,918, filed Nov. 19, 1992, now abandoned, the disclosures of which are herein incorporated by reference.

FIELD OF THE INVENTION

This invention generally relates to a class of nitroaromatic compounds that, when activated by reductive metabolism, bind to hypoxic cells. This reductive metabolism and binding increase as the oxygen concentration of cells decreases, which enables these compounds to be used as indicators of hypoxia. The present invention presents novel nitroaromatic compounds; immunogenic conjugates comprising the novel nitroaromatic compounds and proteins; and monoclonal antibodies specific for the novel nitroaromatic compounds of the invention, their protein conjugates, their reductive byproducts, and adducts formed between mammalian hypoxic cells and the compounds of the invention. The invention is further directed to methods for detecting levels of low oxygen in tissue. Detection may be done directly using methods such as imaging techniques involving specific isotopes attached to the nitroaromatic drug, or indirectly using the monoclonal antibodies (mAbs) in immunohistological assays. Still further, the present invention is directed to kits for performing the methods of the invention.

BACKGROUND OF THE INVENTION

One of the most important goals in oncology is the identification and elimination of treatment resistant cells; hypoxic cells are the most familiar examples of this type of cell. Kennedy, et al., *Biochem. Pharm.* 1980, 29, 1; Moulder, et al., *Int. J. Radioat. Oncol. Biol. Phys.* 1984, 10, 695; Adams, *Cancer*, 1981, 48, 696. Hypoxic cells are seldom found in normal tissues, and are generally found only in conjunction with certain tumors, vascular diseases, or after a stroke.

As certain tumors enlarge, the tissue often outgrows its oxygen and nutrient supply because of an inadequate network of functioning blood vessels and capillaries. Although the cells deprived of oxygen and nutrients may ultimately die, at any given time a tumor may produce viable hypoxic cells. These hypoxic cells, although alive, have very low oxygen concentrations because of their remoteness from the blood vessels.

The level of molecular oxygen has important implications in disease diagnosis and prognosis. In radiation oncology, for example, hypoxic cells in solid tumors are highly resistant to killing by radiation and some forms of chemotherapy. When chemotherapeutic agents are administered to patients the agents are carried through the functioning blood vessels and capillaries to the target tissue. Because hypoxic tissue lacks a fully functioning blood supply network, the chemotherapeutic drugs may never reach the hypoxic cells; instead, intervening cells scavenge the drug. The result is that the hypoxic cells survive and recurrence of the tumor is possible. Kennedy, et al., supra.

Tissue hypoxia also hinders the effectiveness of radiation therapy, especially of neoplasms. Radiation treatment is most effective in destroying oxygen containing cells because oxygen is an excellent radiation sensitizer. The presence of hypoxic cells impedes this treatment because their low oxygen concentration renders the ionizing radiation relatively ineffective in killing the cancerous cells. Therefore, hypoxic cells are more likely to survive radiation therapy and eventually lead to the reappearance of the tumor. The importance of hypoxic cells in limiting radiation responsiveness in animal tumors is well known, Adams, supra; Moulder, et al., supra; Chapman, et al., "*The Fraction of Hypoxic Clonogenic Cells in Tumor Populations*," in *Biological Bases and Clinical Implications of Tumor Radioresistance* 61, G. H. Fletcher, C. Nevil, & H. R. Withers, eds., 1983. Studies have revealed that such resistant cells greatly affect the ability of radiation and chemotherapy to successfully sterilize tumors in animals. Substantial work since that time has shown similar problems in human tumors. Despite the progress in animal studies regarding the identification of hypoxic cells, limited success has been achieved in humans. One reason for this disparity may relate to differences in tumor growth and other host related factors, but in addition, there has been no suitably accurate method to assess tissue oxygen at a sufficiently fine resolution.

Venous oxygen pressure is generally ~35 Torr, an oxygen level providing nearly full radiation sensitivity. As the oxygen level decreases below 35 Torr, radiation resistance gradually increases, with half-maximal resistance at about 3.5 Torr, and full resistance at about 0.35 Torr. Therefore, it is necessary to measure much lower oxygen levels than are usually encountered in normal tissue. Current technology does not meet this need. Oxygen partial pressure measured using current techniques often yields an average value for large numbers of neighboring cells. This is a severe impediment for detection and diagnosis because histological evaluation of solid tumors suggest that important changes in cellular oxygen can occur over dimensions of even a few cell diameters. Urtasun, et al., *Br. J. Cancer*, 1986, 54, 453.

Nitroheterocyclic drugs have been under extensive investigation as oxygen indicators. It is known that this class of compounds has the potential for resolution at the cellular level and can provide sufficient sensitivity to monitor the low oxygen partial pressures described above. This technique involves the administration of nitroaromatic drugs to the tissue of interest. The drugs undergo bioreductive metabolism at a rate which increases substantially as the tissue's oxygen partial pressure decreases. The result of this bioreductive metabolism is that reactive drug products are formed which combine chemically to form adducts with predominantly cellular proteins. Because the metabolic binding of these compounds to cellular macromolecules is inhibited by oxygen, these compounds bind to hypoxic cells in preference to normal, healthy, oxygen-rich tissue. This preferential metabolic binding, or adduct formation, provides a measure of the degree of hypoxia. Koch, et al., *Int. J. Radiation Oncology Biol. Phys.*, 1984, 10, 1327.

Misonidazole, MISO 3-methoxy-1-(2-nitroimidazol-1-yl)-2-propanol, and certain of its derivatives have been under extensive investigation as indicators of hypoxia in mammalian tissue. Chapman, et al., *Int. J. Radiat. Oncol. Biol. Phys.*, 1989, 16, 911; Taylor, et al., *Cancer Res.*, 1978, 38, 2745; Varghese, et al., *Cancer Res.*, 1980, 40, 2165. The ability of certain misonidazole derivatives to form adducts with cellular macromolecules, referred to as binding throughout this application, has formed the basis of various detection methods.

For example, $H^3$ or $C^{14}$ labelled misonidazole has been used in vitro and in vivo, with binding analyzed by liquid scintillation counting or autoradiography. Chapman, 1984 supra; Urtasun, 1986, supra; Franko, et al., *Cancer Res.*, 1987, 47, 5367. A monofluorinated derivative of misonidazole has utilized the positron emitting isotope $F^{18}$ for imaging bound drug in vivo, Rasey, et al., *Radiat. Res.*, 1987, 111, 292. A hexafluorinated derivative of misonidazole has been assayed directly (no radioactive isotopes) via nuclear magnetic resonance spectroscopy (NMR or MRI) techniques. Raleigh, et al., *Int. J. Radiat. Oncol. Biol. Phys.*, 1984, 10, 1337. Polyclonal antibodies to this same derivative have allowed immunohistochemical identification of drug adducts. Raleigh, et al., *Br. J. Cancer*, 1987, 56, 395. An iodine isotope has been incorporated into another azomycin derivative, azomycin arabinoside, allowing radiology techniques of detection. Parliament, et al., *Br. J. Cancer*, 1992, 65, 90.

A fluorescence immunohistochemical assay for detecting hypoxia is described in the literature. Raleigh, et al., 1987, supra. A method for preparing immunogenic conjugates for use in such assays is broadly disclosed in U.S. Pat. No. 5,086,068, issued to Raleigh, et al., on Feb. 4, 1992 ("Raleigh patent"). The Raleigh patent describes a method for preparing an immunogenic conjugate comprising a known fluorinated misonidazole derivative and an immunogenic carrier protein, hemocyanin. The misonidazole derivative used in this method was the hexafluorinated 2-nitroimidazole (CCI-103F) described above in connection with the NMR studies, 1-(2-hydroxy-3-hexafluoroisopropoxy-propyl)-2-nitroimidazole.

The resulting conjugate is used to raise rabbit polyclonal antibodies specific for the misonidazole derivative. Fluorescence immunohistochemical studies showed that the polyclonal antibodies bound to hypoxic (central) regions of spheroids (a multicellular aggregate of cells in tissue culture having some properties more closely related to tumors) and tumor sections in patterns similar to those revealed by audioradiographic studies using radioactive drug alone, i.e. without polyclonal antibodies.

However, polyclonal antibodies are plagued by numerous difficulties involving cross-reactivity, lack of specificity, insensitivity, inability to purify the actual antibodies of interest, and highly unstable supply.

The Raleigh patent's technology, of conjugating a small antigen to a large carrier protein to elicit an immune response, is a central basis of antibody production and is well known in the art. Those skilled in the art would also appreciate that nitroaromatics must be activated by chemical or biochemical reduction to cause adducts to form with cellular macromolecules. Further, it has not been possible to produce monoclonal antibodies using the methods described in the Raleigh patent and paper (Raleigh et al., 1987, supra).

The bioreductive drug assays described above do not directly measure oxygen partial pressure, even though this is the required value, using the example of radiation therapy to predict radiation response. Rather, the assays measure adduct formation, a biochemical process which is inhibited by oxygen. The data generated using these methods has shown that the degree of inhibition by oxygen varies substantially from tissue to tissue. Franko, et al., 1987, supra. Furthermore, the maximum rate of adduct formation in the complete absence of oxygen is also highly variable from tissue to tissue, as is the maximum percentage of inhibition by oxygen, Koch, in *Selective Activation of Drugs by Redox Processes*, Plenum Press, pp. 237–247, Adams, et al., eds, New York, 1990. Another way of expressing these limitations is that the bioreductive formation of nitroaromatics provide only a relative indication of varying oxygen levels, but is inadequate at providing an absolute measurement of oxygen partial pressure because there are several factors which affect adduct formation in addition to changes in oxygen, non-oxygen-dependent factors. Additionally, the choice of nitroaromatic drug affects the variability related to the non-oxygen-dependent factors.

Most research has focused on misonidazole and certain of its derivatives. However, misonidazole is the most susceptible of several drugs tested to non-oxygen-dependent variations in adduct formation. Koch, Selective Activation, supra. Other problems relate to various physicochemical properties of existing drugs, all of which can influence the non-oxygen dependent variations in adduct formation. For example, the hexafluorinated misvonidazole derivative described above had a high degree of insolubility.

Although radiochemical tracers provide a sensitive method for detecting tissue hypoxia, the biohazards and costs associated with these techniques are a significant drawback. The amount of radioactivity associated with the administration of such labelled drugs, which still requires a tissue biopsy, becomes a substantial problem in animal studies and an even greater problem in humans where 30 millicuries of tritiated drug are typically used. Urtasun, et al., 1986, supra. $C^{14}$ is prohibitively expensive and causes unacceptable radiation exposures. The use of radioactive tracers is generally not acceptable because of the stringent requirements associated with handling radioactive tissues and bodily fluids. There are also practical limitations to the use of radioactive tracers. For example, the delay required for audioradiographic analysis of the tissue sections, often several weeks, is a very serious impediment to the rapid analysis required in treatment determination. Moreover, toxicity problems associated with certain misonidazole derivatives resulted in the drug being administered at a relatively low concentration, which decreased detection sensitivity.

The Raleigh patent discloses immunogenic conjugates useful for producing polyclonal antibodies, but data generated using the patent's teachings has produced variable results, problematic in a detection technique. Furthermore, independent experimentation performed according to the Raleigh patent's methods did not reproduce the high degree of conjugation between the misonidazole derivatives and the protein as was claimed.

There is no method currently available that can safely and consistently assay the oxygen level in mammalian tissue. There has been a long felt need for safer and more predictable oxygen detection methods without the concomitant hazards associated with radioactivity. The present invention addresses this need among others. See *Detection of Hypoxic Cells by Monoclonal Antibody Recognizing 2-Nitroimidazole Adducts*, Cancer Res., 1993, 53, 5721–76, the disclosures of which are herein incorporated by reference.

SUMMARY OF THE INVENTION

This invention presents novel nitroaromatic compounds; immunogenic conjugates comprising the novel nitroaromatic compounds and proteins; and monoclonal antibodies specific for the novel nitroaromatic compounds of the invention, their protein conjugates, their reductive byproducts, and adducts formed between mammalian hypoxic cells and the compounds of the invention. The novel compound's protein conjugates, reductive byproducts, and adducts formed between mammalian hypoxic cells and the compounds of the invention may be generally referred to as compositions throughout this application. The novel compounds and compositions of the invention, and the methods according to this invention, provide the basis for sensitive and precise methods for detecting tissue hypoxia.

The compounds of the invention possess unique properties that make them safer and more predictable oxygen indicators than previous compounds. The structure of the parent 2-nitroimidazole, etanidazole, N-(2-hydroxyethyl)-2 (2-nitro-1H-imidazol-1-yl)acetamide, has been shown to be less susceptible to non-oxygen-dependent variations in adduct formation than is misonidazole.

Preferred embodiments of the invention containing 5 fluorines have now been provided which maintain high solubility. A greatly preferred embodiment is 2(2-nitro-1H-imidazol-1-yl)-N-(2,2,3,3,3-pentafluoropropyl)acetamide, referred to as EF5 throughout this application. This increased solubility over misonidazole derivatives currently in use permits administering a higher drug concentration resulting in enhanced detection sensitivity without the toxicity observed with current methods.

Furthermore, the formulation of specific drug-protein conjugates has allowed the formation of monoclonal antibodies against such conjugates produced by cellular bioreductive metabolism. Despite world-wide efforts, monoclonal antibodies have not previously been prepared against any nitroaromatic drug adducts, and it is essential to have a reliable and consistent source of such monoclonal antibodies for any clinical assay. The development of monoclonal antibodies represents a significant advance in technology because of the biohazards associated with the use of radioactive tracers such as $H^3$ and $C^{14}$.

In contrast to the EF5's overall solubility, is the hydrophobicity of its halogenated side chain. This characteristic of the compounds of the invention improves detection efficiency because the side chain's hydrophobic nature causes a greater proportion of macromolecular adducts to form between the drug-protein conjugate and the hypoxic cell proteins than would be the case for more hydrophilic derivatives. The relatively large number of fluorines enhances any assay of this atom, with $F^{19}$ preferred for magnetic resonance imaging (MRI) and $F^{18}$ for positron emission tomography (PET). These competing properties are unique to the compounds of the invention and add to the novelty and utility of the invention.

Further, the side chain of the present compounds is highly non-physiological, which is believed to contribute to their antigenic characteristics. The monoclonal antibodies of this invention are highly specific for the novel nitroaromatic compounds of the invention, their protein conjugates, their reductive byproducts, and adducts formed between mammalian hypoxic cells and the compounds of the invention. This specificity makes these antibodies superior detectors than the polyclonal antibodies currently used in the art. As indicated above, a consistent source of identical antibodies is required for clinical assays. The novel compounds of the invention provide the basis for a sensitive, versatile, and more accurate method for detecting tissue hypoxia.

Thus, the present invention presents a novel class of compounds, similar in core structure to misonidazole but having new side chains that make them much more predictable oxygen indicators and much more amenable to immunohistochemical and other assays. The novel compounds and compositions of the invention and the corresponding methodologies provide techniques for measuring the degree of hypoxia in mammalian tumors with a precision and sensitivity that has not been achieved before. These novel compounds and compositions may be used to detect hypoxia using standard nuclear medical procedures with a consistency not previously observed in the art. These novel compounds also provide the basis for immunological assays.

The novel class of compounds of this invention are halogenated 2-nitroimidazole derivatives capable of stimulating the immunogenic process and enabling the production of monoclonal antibodies specific for the compounds of the invention, their protein conjugates, reductive byproducts, and adducts formed between mammalian hypoxic cells and the compounds of the invention. The compounds of the present invention have the general structure depicted below

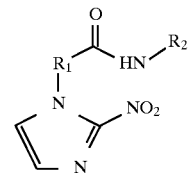

wherein $R_1$ may be either $CH_2$, $CHX$, or $CX_2$, where X is a halogen atom. The $R_2$ substituent is an alkyl group containing 1 to 6 carbons, and preferably having up to about 6 halogen atoms. The preferred halogen atom is fluorine. In accordance with preferred embodiments, compounds of the invention will have about 5 fluorine atoms, $R_1$ will be $CH_2$ and $R_2$ will be $CH_2CF_2CF_3$. The invention further presents compositions comprising the novel compounds of the invention bound to a protein. These drug-protein conjugates are capable of eliciting an immune response that enables the production of monoclonal antibodies highly specific for the compounds of the invention; their reductive byproducts, protein conjugates, and adducts formed between tissue proteins and the compounds of the invention. The monoclonal antibodies' specificity for the claimed compounds and compositions provides the basis for sensitive, accurate, and precise immunohistochemistry-assay-based detection of hypoxia. In a preferred embodiment of the invention, the protein carrier may be albumin, Bowman Birk inhibitor, or lysozyme. In another preferred embodiment, the protein is lysozyme, $R_1$ is $CH_2$, and $R_2$ is $CH_2CF_2CF_3$. In a more preferred embodiment, the protein is Bowman Birk inhibitor (BBI), $R_1$ is $CH_2$, and $R_2$ is $CH_2CF_2CF_3$.

The invention is further directed to pharmaceutical formulations of the novel drug compounds. In accordance with preferred embodiments, a compound of the invention is dissolved or dispersed in a pharmaceutically acceptable diluent. Preferred diluents are non-pyrogenic physiological saline.

The invention is also directed to formulations of immunogenic conjugates comprising the novel drug compounds of the invention bound to a protein carrier and dissolved or dispersed in a diluent.

In another aspect of the invention, monoclonal antibodies specific for the compounds of the invention, their protein conjugates, reductive byproducts, and adducts formed between mammalian hypoxic cells and the compounds of the invention are provided. The protein conjugates, reductive byproducts, and adducts formed between mammalian hypoxic cells and the compounds of the invention are referred to generally as compositions. In a preferred embodiment of the invention, monoclonal antibodies will be specific for compounds and compositions of the invention where the halogen atom is fluorine. In a more preferred embodiment of the invention, the monoclonal antibodies will be specific for compounds and compositions having about 5 fluorine atoms. In yet a more preferred embodiment, the monoclonal antibodies will be specific for compounds and compositions of the invention where $R_1$ is $CH_2$. In another preferred embodiment, the monoclonal antibodies of the invention will be specific for the compounds and compositions of the invention where $R_2$ is $CH_2CF_2CF_3$.

In a still more preferred embodiment, the monoclonal antibodies will be specific for compounds and compositions where $R_1$ is $CH_2$ and $R_2$ is $CH_2CF_2CF_3$. Methods for preparing the monoclonal antibodies are also provided. As will be appreciated, the monoclonal antibodies of the invention can be either to the novel compounds per se or to the compounds bound to a protein.

In a further aspect of the invention, methods for assaying tissue hypoxia are provided. A tissue sample is assayed using immunohistochemical techniques or imaging techniques. Imaging techniques may be used for non-invasive analysis. Imaging methods comprise using the novel compounds of the invention without immunohistochemical assays, and preferably without the use of monoclonal antibodies to detect hypoxic cells. The mammal is administered a compound of the invention, dissolved or dispersed in a suitable pharmaceutical carrier or diluent, as discussed above. The compound is allowed to clear from the mammal, and then a portion of the mammal containing the tissue of interest is analyzed non-invasively such as through magnetic resonance imaging (MRI) or positron emission tomography (PET). A proportion of the compound will remain in the body, bound or associated with hypoxic cells. In the case of MRI, conventional non-radioactive ($F^{19}$) isotopes of fluorine are used. In the case of PET, a compound of the invention must first be formulated with the positron emitting isotope $F^{18}$.

In another preferred embodiment of the invention, the assay methods use immunochemistry. These methods generally comprise administering to a mammal, as above, a compound of the invention; obtaining a tissue sample; and detecting the presence of adducts formed between cells of the sample and a compound of the invention by contacting the tissue sample with the invention's monoclonal antibodies associated with a detection system. The mAb will be specific for the adduct; that is, the mAb will be specific for the adduct formed between tissue proteins and the compound previously administered. The degree of tissue hypoxia is determined by quantifying the level of antibody interaction with the cells such as by using enzyme linked immunosorbant assay (ELISA), microdialysis, immunohistochemical staining, or other immunological protocols.

Yet another embodiment of the invention requires that the drug-hypoxic tissue adducts be detected in situ. A compound of the invention is administered to a mammal and allowed to clear from the non-binding tissue. A labelled mAb specific for the adduct; that is, an mAb specific for an adduct formed between tissue proteins and the drug previously administered, is administered. The antibody is labelled with isotopes suitable for radiographic or nuclear medicine assays and will bind to the adducts formed with the hypoxic tissues. The advantages of this embodiment are that the antibodies can be used in a non-invasive assay of the tissue, there being more flexibility in the labelling of the antibody than in the labelling of the 2-nitroimidazole drug, whose structure is relatively fixed.

Kits useful for diagnostic applications comprising the novel compounds or compositions are also within the ambit of the present invention. These kits include a drug formulation of the invention, along with immunochemical reagents, especially including monoclonal antibodies of the invention.

BRIEF DESCRIPTION OF THE DRAWINGS

In FIGS. 5 and 6, a mAb of the invention was unmodified and a second antibody (goat anti-mouse-IgG1 labelled with the fluorescent dye fluorescein) was used to monitor the reaction. FIG. 5 shows that tissue culture cells, 9L rat glioma, were stained much more heavily when incubated with a compound of the invention under hypoxic than under aerobic conditions. FIG. 6 shows the same effect, except incubating a multicellular spheroid culture of mouse EMT6 cells with a compound of the invention. In this system, hypoxia is produced by metabolic depletion of oxygen by the outer cells leaving an inner annulus of hypoxic viable cells, and an inner core of anoxic, necrotic cells. The outer, unstained band represents viable oxygenated cells. FIG. 7 shows that hypoxic cells in vivo can be analyzed in a similar manner after biopsy of a tumor specimen. In this case, EF5 was administered to a live tumor-bearing animal. A tissue section from a tumor biopsy was stained with a mAb of the invention which had been modified with the addition of a fluorescent dye (AMCA). The heavily staining, bright regions depict areas of high binding of the compound of the invention.

FIG. 11 tests the prediction discussed above in connection with FIG. 10 using the multicellular spheroid model (as previously discussed). Spheroids, grown in spinner flasks, are aggregated of several hundred thousand cells which develop hypoxic, radioresistant cells at their centers as a result of diffusion gradients of oxygen. These gradients are imposed by oxygen consumption of cells at the periphery of the spheroids, and have a genesis very much like those found in tumors. The hash-marked curve shows that flow cytometric analysis of cells from spheroids incubated with 100 $\mu$M 2-(2-nitro-1H-imidazol-1-yl)-N-(2,2,3,3,3-pentafluoropropyl) acetamide (EF5) in their "natural" growth state (i.e., the gas phase of the spinner flask contains air). The continuous-line curve illustrates the flow cytometric analysis of identically treated spheroids in an "oxygen supplemented" state (i.e., extra oxygen was added to the gas phase of the spinner flask). The flow cytometric analysis predicts that the "oxygenated supplemented" spheroids should be more radiation sensitive than those grown in their natural state.

FIG. 15C shows binding of EF3, 2-(2-nitro-1H-imidazol-1-yl)-N-(3,3,3-trifluoropropyl) acetamide, (the trifluoro analogue of EF5) administered via an intravenous injunction at 100 $\mu$M whole-body to an EMT6-tumor-bearing mouse. EF3 is similar to EF5 but has only three fluorines at the terminus of the side-chain. Binding of EF3 was monitored by monoclonal antibodies to this drug. Note that very similar types of variations in drug binding can be found using either drug.

Figure 1:
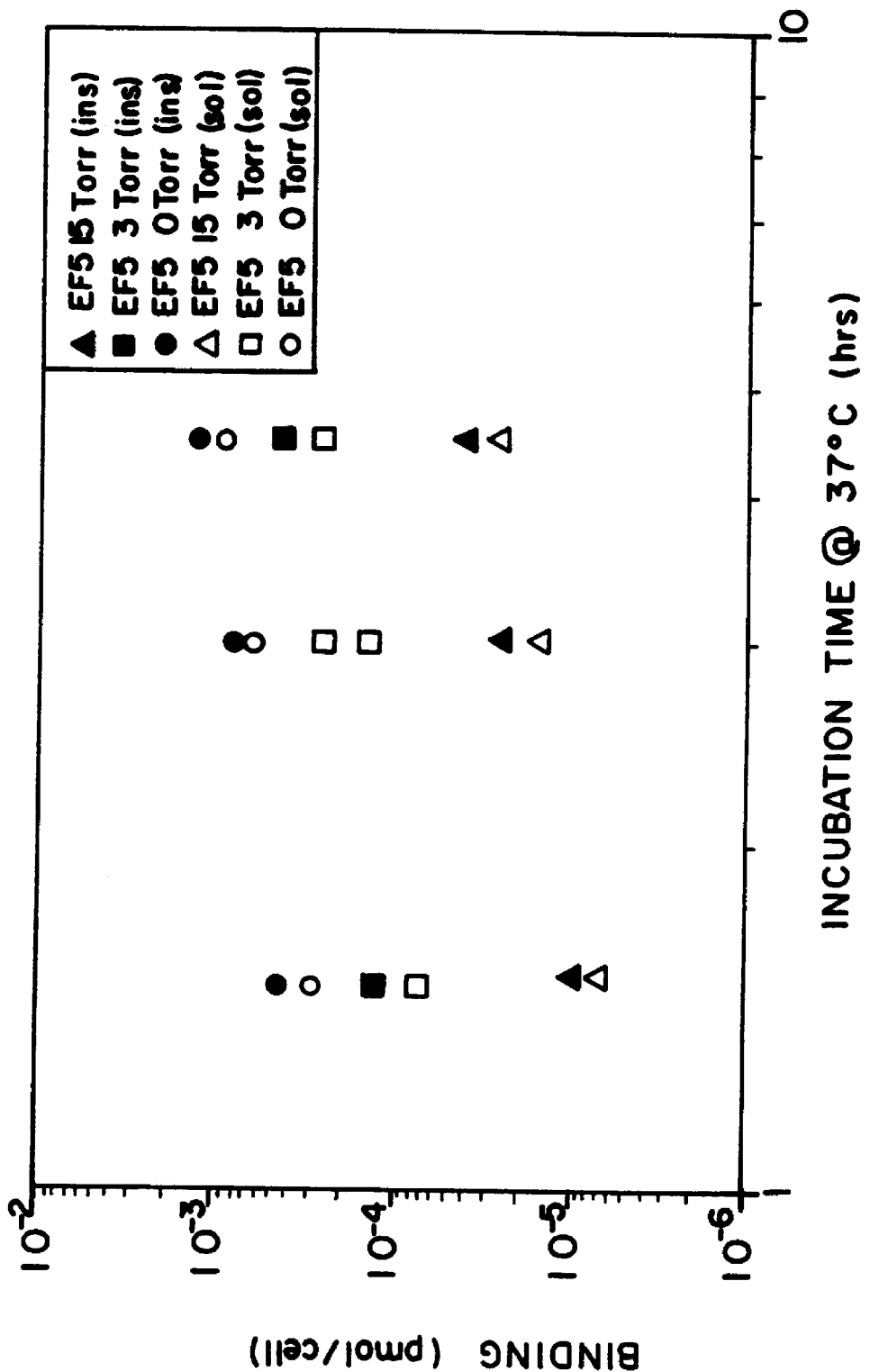
FIG. 1 depicts a compound of the invention binding to cells in a manner which increases substantially as the oxygen concentration decreases. Binding was detected using a radioactive form of a specific compound of the invention, EF5. The graph symbols are defined as follows: circles represent hypoxic cells; squares represent cells containing an intermediate level of oxygen (~3 Torr); and triangles represent cells containing a higher level of oxygen (15 Torr). In each case the solid symbols are for trichloroacetic acid (TCA) precipitable adducts, and the open symbols are for TCA soluble adducts. The cells in this experiment were 9L glioma cells.

For all Figures, tissue sections are roughly 1000 $\mu$m×600 $\mu$m, 14 $\mu$m thickness.

DETAILED DESCRIPTION OF PREFERRED EMBODIMENTS

Hypoxic cells in solid tumors have been associated with treatment resistance by radiation, Moulder, supra, and some forms of chemotherapy, Kennedy, supra. Because of this effect, there is a great oncological need to identify hypoxic cells. In view of the foregoing, it is highly desirable to be able to assay for the presence of hypoxic cells in an animal or human tumor. However, there is no method currently available that can safely and consistently assay the oxygen level in mammalian tissue. The compounds and methods of the claimed invention address this need in the art.

The present invention provides a novel class of 2-nitroimidazole derivatives that are predictable oxygen indicators using both immunohistochemical assays and imaging techniques, said compounds having the structure:

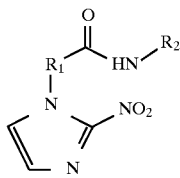

where $R_1$ is $CH_2$, CHX, or $CX_2$ where X is a halogen atom; and $R_2$ is $C_1$ to $C_6$ alkyl having up to about 6 halogen atoms.

The compounds of the invention are very useful in detecting oxygen levels because of their dramatic specificity for hypoxic cells over normal, healthy, oxygenated tissue. Another aspect of the invention provides immunogenic conjugates comprising the novel compounds and a protein, and monoclonal antibodies specific for the novel compounds of the invention, their protein conjugates, reductive byproducts, and adducts formed between mammalian tissue proteins and the compounds of the invention. Methods for detecting tissue hypoxia are also provided.

When hypoxic cells and aerobic cells are incubated in the presence of compounds of the invention, the monoclonal antibodies of the invention selectively bind to hypoxic cells to a great degree. See FIGS. 1, 5–7. This preferential binding provides the basis for assaying tissue hypoxia in mammals.

Compounds of the invention can be synthesized using various reaction conditions depending on the starting material and ultimate requirements. For example, making of PET isotope-containing derivatives requires rapid addition of the $F^{18}$ moiety followed by immediate purification and use because of the short half-life of $F^{18}$, 103 minutes.

Generally, the compounds of the invention are synthesized under the following reaction conditions. The reaction may be performed in anhydrous tetrahydrafuran (THF) under argon and in the presence of iso-butylchloroformate and N-methylmorpholine. The staring material may be an alcohol derivative of 2-(2-nitro-1H-imidazol-1-yl) acetamide. The acetamide undergoes alkaline hydrolysis at the carbonyl group to yield an acid derivative of the 2-(2-nitro-1H-imidazol-1-yl). This is followed by nucleophilic substitution of a halogenated alkylamine at the acid intermediate's carbonyl group, to yield a halogenated nitroimidazole acetamide.

Alternatively, the starting material may be a 2-nitroimidazole acid derivative, which eliminates the need for the basic hydrolysis. The acid derivative then undergoes nucleophilic substitution with a halogenated alkylamine at the acid's carbonyl group to yield a halogenated nitroimidazole acetamide. Other synthetic methods will be apparent to those skilled in the art.

The reaction may yield a reaction slurry from which the product must be recovered. Methods of recovering the sample include any filtration or separation techniques known in the art. Such methods include, but are not limited to, vacuum filtration, separatory extraction, or distillation. A preferred method is filtration using air or liquid, but other methods will be apparent to those skilled in the art.

The filtration solid may further require washing with organic solvents to separate out impurities or other reaction intermediates or byproducts. Organic solvents include, but are not limited to, ether, methanol, ethanol, ethyl acetate, or hexanes. Ether is a preferred solvent, but other types of solvents will be apparent to those skilled in the art. Any organic solvent should be evaporated using methods known in the art. Evaporation methods may be accomplished at room temperature, by vacuum, aspiration, or by using latent heat. The evaporation methods are not limited to these techniques and other techniques will be apparent to those skilled in the art.

The reaction product is then purified using purification techniques known in the art. These techniques include, but are not limited to, column chromatography, flash chromatography, recrystillization, or gel chromatography. When using chromatographic purification methods, gradient elution is preferred. Combinations of organic solvents include, but are not limited to, methanol, acetonitrile, hexanes, carbontrichloride, and ethyl acetate. Other purification methods will be apparent to those skilled in the art.

In certain embodiments, the halogen atom of the compounds and compositions will be fluorine. In a more preferred embodiment, the compounds and compositions of the invention will have up to about 6 fluorine atoms. In accordance with other preferred embodiments, $R_1$ will be $CH_2$. In another preferred embodiment, $R_2$ will be an alkyl group containing about 1 to 6 carbons and will have up to about 6 halogen atoms, preferably fluorine. In a more preferred embodiment of the invention, $R_1$ will be $CH_2$ and $R_2$ will be $CH_2CF_2CF_3$. This compound is referred to as EF5 throughout the application.

This invention is further directed to drug-protein conjugates formed between a compound of the invention and a suitable carrier protein, these compositions are referred to as antigens throughout this application. Antigens prepared using technology known in the art did not produce active mAbs, so previous procedures were substantially modified.

The prior art relates that antigen-forming reactions may be carried out between pH 4 to 7. It has now been found that these conditions fail to produce a sufficient number of drug-protein conjugates. It is greatly preferred to carry out the antigen-forming reactions at neutral or higher pH, preferably near neutrality. Under these conditions the drug-protein conjugation is much more efficient.

The conjugation process is also much more efficient when the carrier protein contains cysteine sulfhydryl groups (PSH). Unfortunately, the cysteine residues of most proteins are a) few in number (e.g., hemocyanin); b) are not accessible (e.g., alcohol dehydrogenase); or c) are oxidized as cystine dimers which do not bind reduced nitroaromatics. Although cystine dimers of several proteins can be very efficiently reduced via a radiochemical chain reaction, Koch & Raleigh, *Arch. Biochem. Biophys.*, 1991, 287, 75, the resulting modified protein is often insoluble possibly because of the formation of disulfide bridges between molecules. It was not possible to reduce the protein cystines by addition of excess quantities of agents such as dithiothreitol or mercaptoethanol, which can simultaneously reduce and stabilize cystine-containing proteins, because then adducts would preferentially form with the excess low-molecular weight thiol. Thus it was convenient to identify a protein with high cystine content, and having relative freedom from precipitation on radiochemical reduction. Bowman Birk Inhibitor, a trypsin/chymotrypsin inhibitor from soybeans, (Bowman Birk Inhibitor (BBI)—7 cystine bridges, molecular mass 7800) was found to have near optimal characteristics from this point of view, and reduction of up to an average of 8 cysteine residues was possible. The EF5-BBI conjugates were then made in a second radiochemical reduction step.

Oxygen is excluded from the solutions using techniques previously described in Koch & Raleigh, *Arch. Biochem. Biophys.*, supra. Glass containers with specially constructed ceramic-enclosed spin bars to eliminate oxygen released from teflon, Franko, et al., "*Recent Results in Cancer Res.*

95" in *Culture of Cellular Spheroids* 62 (Verlag 1984), were placed into leakproof aluminum chambers, and the oxygen-containing air was replaced by nitrogen using a number of gas exchanges.

Suitable protein carriers include, but are not limited to, albumin (ALB), lysozyme (LYZ), and Bowman Birk inhibitor (BBI). In a more preferred embodiment of the immunogenic conjugate, the drug is EF5 and the protein is either BBI or LYZ.

This invention is also directed to monoclonal antibodies that are highly specific for the compounds of this invention, their protein conjugates, reductive byproducts, and adducts formed between mammalian tissue proteins and the compounds of the invention. The drug-protein conjugate prepared according to the aforementioned procedure is used to elicit antibody formation. When a drug-protein conjugate of the invention is bound to a protein carrier in vitro and administered to a mammal, monoclonal antibodies specific for compounds of the invention, their protein conjugates, reductive byproducts, and adducts formed between mammalian hypoxic cells and the compounds of the invention can be raised. The preparation of monoclonal antibodies is known in the art. Particularly, Kohler and Milstein's method, Kohler, et al., *Nature*, 1975, 256, 495, with modifications as described in Knauf, et al., *Cancer Immunol. Immunotherapy*, 1986, 21, 217–225.

Generally, the drug-protein conjugate compositions were used to immunize mice using conventional techniques. See generally Knauf, et al., supra. A host is injected with a drug-protein conjugate of the invention, serving as antigen to elicit an immune response. After an appropriate incubation period, blood is drained from the host and analyzed. When it was found that the host's serum showed strong activity against the antigen, the animal was sacrificed and its spleen cells used to make hybridoma clones.

There are well-known methods to raise such antibodies. Thus, the host's spleen can be removed and the immune cells fused with appropriate myeloma cells to form a hybridoma using technology known in the art. Kohler, et al., supra. Such hybridomas are capable of producing monoclonal antibodies specific for the drug of the particular drug-protein conjugate administered to the mammal. Kohler, et al., supra. In a preferred embodiment of the invention, the hybridoma clone will be conditioned to grow in serum-free medium. This ability to grow in serum-free medium permits facile purification of the antibodies and the easy addition of detection moieties as a fluorophore, biotin, or an enzyme.

ELK-2 cells were conditioned to grow in serum free medium by slowly adapting them to lower and lower levels of serum, using a special medium formulation. See U.S. Pat. No. 4,816,401, issued to Taupier & Lord, 1989.

The drug compounds of the invention are very useful in detecting oxygen levels because of their dramatic specificity for hypoxic cells over normal healthy oxygenated tissue. When hypoxic cells and aerobic cells are incubated in the presence of the new novel compounds, the monoclonal antibodies of the invention selectively bind to hypoxic cells. This preferential binding provides the basis for assaying tissues in mammals.

For purposes of the current invention, mammals include, but are not limited to the Order Rodentia, such as mice; Order Logomorpha, such as rabbits; more particularly the Order Carnivora, including Felines (cats) and Canines (dogs); even more particularly the Order Artiodactyla, Bovines (cows) and Suines (pigs); and the Order Perissodactyla, including Equines (horses); and most particularly the Order Primates, Ceboids and Simoids (monkeys) and Anthropoids (humans and apes). The preferred mammals are humans.

Methods of detecting tissue hypoxia in mammalian tissue include, but are not limited to non-invasive imaging techniques and immunohistochemistry. Imaging techniques include, but are not limited to single photon emission computed tomography (SPECT), PET, and nuclear magnetic resonance imaging, usually called magnetic resonance imaging (MRI). Generally, imaging techniques involve administering a compound with marker atoms which can be detected externally to the mammal. A compound of the invention, is dissolved or dispersed in a pharmaceutically acceptable diluent, such as non-pyrogenic physiological saline, is administered to the mammal; time is allowing to clear non-metabolized compound; and tissue hypoxia is assayed using detectors of the marker atoms.

In a preferred embodiment of the invention, the compound will have at least 5 fluorine atoms. In a more preferred embodiment, of the invention $R_1$ will be $CH_2$. In yet a more preferred embodiment, $R_2$ will be $CH_2CF_2CF_3$. In a still more preferred embodiment, $R_1$ will be $CH_2$ and $R_2$ will be $CH_2CF_2$ $CF_3$, yielding the compound EF5. Using PET the preferred isotope is $F^{18}$, using MRI the preferred isotope is $F^{19}$.

In another preferred embodiment of the invention, the detection techniques utilize the monoclonal antibodies and immunohistochemistry. These techniques include, but are not limited to, immunoblotting or Western blotting, ELISA, sandwich assays, fluorescence, biotin or enzymatic labeling with or without secondary antibodies. Generally, immunohistochemistry involves staining cryosectioned tissue samples. A mammal is injected with a compound of the invention dispersed or dissolved in a pharmaceutically accepted diluent. The compound selectively binds to the tissue proteins of hypoxic cells to form an adduct. A sample of tumor tissue is obtained and assayed using the invention's monoclonal antibodies in conjunction with known immunohistological techniques. The degree of binding of the antibodies to the side chain of the adduct provides a measurement of the degree of hypoxia in the tumor tissue. See FIGS. 5–7. In a preferred embodiment of the invention, the monoclonal antibodies of the invention can be used with cells or tissue sections fixed in paraformaldehyde. See FIGS. 6 and 7.

Methods of obtaining tissue samples for analysis, include any surgical and nonsurgical technique known in the art. Surgical methods include, but are not limited to biopsy such as fine needle aspirate, core biopsy, dilation and curettage.

Diagnostic kits are also within the scope of this invention. Such kits include monoclonal antibodies that can rapidly detect tissue hypoxia; and include a compound of the invention, individual or mixed monoclonal antibodies against adducts formed between a compound of the invention and tissue proteins. Preferably, standards of manufactured protein adducts to be used as calibration sources for the assays are also included.

Preferred aspects of the invention are discussed in the following examples. While the present invention has been described with specificity in accordance with certain of its preferred embodiments, the invention is limited only in accordance with the appended claims.

EXAMPLE 1

Synthesis of EF5

EF5, 2(2-nitro-1H-imidazol-1-yl)-N-(2,2,3,3,3-pentafluoropropyl)acetamide, was synthesized using 2-(2-nitro-1H-imidazol-1-yl)acetic acid as starting material. Nucleophilic substitution of a halogenated alkylamine (2,2, 3,3,3-pentafluoropropylamine hydrochloride) at the acid's carbonyl group was effected in anhydrous tetrahydrafuran (THF) under argon in the presence of isobutylchloroformate and N-methylmorpholine. Redistilled N-methylmorpholine (128 μl, 1.17 mmol) was added to 2-(2-nitro-1H-imidazol-1-yl)acetic acid (200 mg, 1.17 mmol) dissolved in anhydrous THF (20 cc) under argon at 0° C. followed 10 minutes later by fresh isobutylchloroformate (167 μl, 1.287 mmol). After 30 minutes at 0° C., a preformed solution of 2,2,3,3,3-pentafluoropropylamine hydrochloride (237 mg, 1.287 mmol) and redistilled N-methylmorpholine (142 μl, 1.287 mmol) in anhydrous THF (2 cc) was added to the creamy solution and the mixture stirred at room temperature for 3 hours. The reaction mixture was then filtered, the solid residue washed with ether and the combined organic solvents evaporated to give a pale yellow solid. Purification by column chromatography (silica gel, 3% MeOH/CHCl$_3$) gave 2(2-nitro-1H-imidazol-1-yl)-N-(2,2,3,3,3-pentafluoropropyl)acetamide as a white crystalline solid which recrystallized from EtOAc/hexanes, mp=136°–137° C.

EXAMPLE 2
Antigen Production

Antigens were formed by radiation-induced covalent binding of EF5 to a protein carrier in an oxygen free environment. Oxygen was excluded from the solutions using techniques previously described in Koch & Raleigh, 1991, supra. Glass containers with specially constructed ceramic-enclosed spin bars to eliminate oxygen released from teflon, Franko, et al., 1984, supra, were placed into leakproof aluminum chambers, and the oxygen-containing air was replaced by nitrogen using a series of gas exchanges. The time for oxygen removal was measured using a polarographic oxygen sensor, as discussed in U.S. Pat. No. 5,030,036 issued to Koch in 1991, enclosed in a nitrogen-flushed container of similar geometry to those used inside the chambers. The chambers were placed above stirring plates (Wheaton Biostir 4) during the oxygen removal process which took about three hours at a stirring rate of 4–5 Hz. Antigen formation was accomplished in a multistep process, each step consisting of a radiochemical reduction of protein disulfides in the absence of EF5, then addition of EF5 followed by a radiochemical induction of adduct formation between EF5 and the reduced proteins. All irradiations were performed under anaerobic conditions, since even traces of oxygen inhibit the necessary reactions. The hypoxic solutions were irradiated in a Shepherd irradiator (Mark 1, Model 30) at a dose rate of approximately 10 Gy per minute at room temperature.

High efficiencies of adduct formation are obtained only at substantially neutral pH. The EF5 was reductively bound to a protein in a solution containing 25–100 mM ammonium formate and 5–10 mM phosphate, pH 7.5. The formate serves to convert oxidizing radicals from the radiation, which can interfere with the desired reduction reactions, into carbon dioxide anion radicals which are also reducing in character. Several proteins, each containing relatively large mole-fractions of cystine were considered: albumin (ALB), molecular mass 67000, 17 cystine cross links; lysozyme (LYZ), molecular mass 14000, 4 cystine cross links; Bowman Birk inhibitor (BBI), molecular mass 7800, 7 cystine cross links and RNAase, molecular mass 14000, 4 cystine crosslinks. The preferred protein was found to be BBI.

A typical cycle involved deoxygenating the protein (2 mg/cc, in 50 mM ammonium formate, 2.5 mM potassium phosphate), reducing protein cystine cross links by irradiating under hypoxia with sufficient dose to reduce about 50% of the cystine residues (typically 20–50 Gy), opening chambers and adding EF5 (150 micromolar), a second deoxygenation followed by sufficient radiation dose to reduce the drug (850 Gy), and ending with a purification/protein concentration step (centrifuge at 5000 G with molecular filter—Centricon 2). Overall recovery of initial protein was 30–50%. A small amount of radioactive EF5 ($C^{14}$-labelled in 2 position of nitroimidazole; specific activity 70 microcurie/mg) was included to keep track of the fraction of drug bound (initial specific activity of radioactivity in protein-containing solution minus specific activity of centricon filtrate).

After 3–5 cycles, the final protein concentration was determined (Pierce BCA assay). The specific activity of adducts was determined by precipitating a small amount of protein with 5% TCA, then dissolving in base. Following the aforementioned procedure results in about 1 conjugate per 3–4 lysozyme molecules, 1–3 BBI molecules, and 0.2–0.5 albumin molecules.

EXAMPLE 3
Preparation of Monoclonal Antibodies

Monoclonal antibodies are prepared by injecting intramuscularly two C57Br/cdJ×SJL/Br (H-2k) mice with 0.05 cc of the antigen at each of two sites, (300 μg protein/cc; antigen conjugate to protein ratio was 0.5:1) emulsified with an equal volume of Freund's complete adjuvant. A booster injection of 0.1 ml antigen in Freund's incomplete adjuvant was given i.p. two months later. Three weeks after the booster injection, a blood sample was taken, allowed to clot and the serum removed and tested using an ELISA assay.

The serum was characterized for its ability to react with the nitroimidazole compound using an ELISA assay technique. Protein or EF5-conjugated protein was allowed to adhere to 96-well an ELISA plates (50 ng protein/well) and additional binding sites subsequently blocked with BLOTTO-Tween® (5% nonfat milk, 0.2% Tween-20) for 60 minutes at 37° C. Antisera dilutions were added and incubated for 45 minutes at 37° C., unbound antibody was removed by washing 3× with 0.02% Tween-20 in PBS and 2× with PBS. To each well was added 0.1 cc of biotinylated horse anti-mouse IgG1 diluted in PBS and incubated for 45 minutes at 37° C., then washed as above. An avidin-biotin peroxidase complex (Vectastain ABC Reagent) diluted in PBS containing 0.1% Tween 20 was added and incubated for 45 minutes at 37° C. The wells were then washed 5× as above. Each well then received 0.05 cc of horseradish peroxidase substrate (0.05 mg/cc OPD [o-phenylenediamine dihydrochloride] in 50 mM citrate/phosphate buffer, pH 4.5, 0.015% hydrogen peroxide). The color was allowed to develop at room temperature for 5–30 minutes, then the reaction was stopped by adding 0.05 cc of 4N $H_2SO_4$. Finally, the optical density was recorded at 490 nm.

A mouse whose antiserum reacted with the EF5 whether it was conjugated to either the immunizing protein (BBI) or other proteins (ALB, LYZ) was selected. This mouse received additional intraperitoneal injections of EF5-protein conjugate (80 μg) at four, three, two and one days before sacrifice and spleen removal. The fusion was performed as described in Harwell, et al., *J. Immunol. Methods*, 1984, 66, 59. The polyethylene glycol (PEG) used was Sigma #P7777 prepared at 35% in serum-free media/5% dimethylsulfoxide (DMSO) and the pH adjusted to 7.4 with 4N NaOH. All cells and reagents were warmed to 37° C. prior to the fusion. After the fusion, the cells were bulk cultured in a roller bottle for two days. The cells were then centrifuged, resuspended in 10 cc of freezing medium (culture medium with 40% fetal bovine serum ~S and 10% DMSO) and frozen at 1 cc per vial.

One vial of the fusion was subsequently thawed and cultured in 5 each 96-well microliter plates in 10% FBS, HAT-containing culture medium (1.36 mg/cc hypoxanthine, 0.038 mg/cc aminopterin, 0.0176 mg/cc thymidine) to select for fused cells, with 2000 irradiated mouse peritoneal cells per well as feeder cells. Wells were screened for specific antibody-producing cells using the ELISA assay described above and BBI and BBI-F5E conjugate as antigens. Six hybridomas were selected based on the differentiation of these two antigens, and were further screened against a panel of additional antigens. One of these, ELK-2-4,3,4 (ELK-2), was selected based on its strong selective reaction against protein-EF5 conjugates and lack of reactivity against any other antigens tested, including whole cell protein preparations. See Table 1 (row 1) and FIGS. 2–4.

EXAMPLE 4
Binding of EF5 to Cells in Tissue Culture Under Defined Oxygen Conditions.

Cells were thawed from frozen stock on a roughly semi-annual basis and tests were made routinely to ensure that the cultures were free from mycoplasma and other contaminations. The cells were cultured (37° C., 95% air+5% carbon dioxide, 100% relative humidity) in the exponential phase of growth by twice weekly transfers using Eagle's Minimal Essential medium containing 12.5% v/v fetal calf serum and antibiotics (all culture solutions from GIBCO). On the day before an experiment, cells were trypsinized and plated onto glass Petri dishes—approximately 200,000 cells confined to the central area of the dish followed by overnight incubation at 37° C. as described previously. Koch, *Radiat. Res.*, 1984, 97, 434.

TABLE 1

ELISA Assay: 10% Portion of 3rd Fusion (Anti EF5-Lysozyme) vs ELK-2 (Anti EF5-BBI)

| Hybridoma | BSA | BSA-EF5 | Lys | Lys-EF5 | BBI | BBI-EF5 | 9L/Control | 9L-EF5 | EMT6/Control | EMT6-EF5 |
|---|---|---|---|---|---|---|---|---|---|---|
| ELK2-4,3,4 | 0 | >2 | .01 | .18 | 0 | >2 | 0 | >2 | .01 | 1.02 |
| ELK 3-5.17 | 0 | >2 | .01 | 1.26 | 0 | >2 | 0 | 0.44 | .02 | 0.26 |
| ELK 3-23 | 0 | >2 | 0 | .86 | 0 | >2 | .03 | 0.41 | .04 | 0.25 |
| ELK 3-29 | 0 | >2 | 0 | 0.20 | 0 | >2 | 0 | 0.05 | 0 | 0.03 |
| ELK 3-2.9 | .01 | .01 | >2 | >2 | 0 | 0.01 | 0 | 0 | 0 | 0 |
| 3-40 | .01 | >2 | >2 | >2 | 0 | >2 | .01 | 0.05 | .02 | .05 |
| 3-41 | 0 | >2 | 0 | 0.01 | 0 | 1.02 | 0 | 0.07 | .01 | .04 |
| 3-42 | 0 | >2 | >2 | >2 | 0 | >2 | 0 | 0.13 | 0 | .08 |
| 3-43 | 0 | >2 | >2 | >2 | 0 | >2 | 0.01 | 0.70 | .01 | .44 |
| 3-44 | 0 | >2 | >2 | >2 | 0 | >2 | 0.01 | 0.14 | .02 | .10 |
| 3-45 | 0 | >2 | >2 | >2 | 0 | >2 | 0.01 | 0.07 | .02 | .08 |
| 3-46 | 0.01 | 0.65 | >2 | >2 | .01 | 0.59 | 0 | 0.02 | .01 | .03 |
| 3-47 | 0 | 0.13 | .02 | 0.07 | 0 | 0.30 | 0 | 0.01 | 0 | .02 |
| 3-48 | 0 | >2 | >2 | >2 | 0 | >2 | 0 | 0.02 | 0 | .01 |
| 3-49 | 0.01 | 0.12 | >2 | >2 | 0.01 | 0.17 | 0.04 | 0.03 | 0.05 | .05 |
| 3-50 | 0 | >2 | 0 | 0.56 | 0 | >2 | 0 | 0.16 | 0.01 | 0.11 |
| 3-51 | 0 | >2 | 0.01 | 0.12 | 0 | >2 | 0.01 | 1.86 | 0.02 | 1.60 |
| 3-52 | 0 | 0.05 | 0.01 | 1.68 | 0 | 0.03 | 0 | 0.03 | 0 | .02 |
| 3-53 | 0 | >2 | 1.33 | >2 | 0 | >2 | 0.01 | 0.05 | 0 | .04 |
| 3-54 | 0.01 | >2 | 0 | 0.14 | 0 | >2 | 0 | 0.05 | 0 | .04 |
| 3-550 | 0 | >2 | 0.07 | 0.28 | 0 | >2 | 0 | 0.04 | 0 | .04 |
| 3-56 | 0 | >2 | 0 | 0.25 | 0 | >2 | 0 | 0.07 | 0 | 0.05 |

MAbs from the most differentially specific clone, designated as ELK-2, were then characterized. Although MAbs from ELK-2 reacted strongly with the parent 2-nitroimidazole, almost no reactivity was found with other nitroheterocyclics. For example, no measurable reactivity was observed for etanidazole at 1000 fold higher concentrations; etanidazole differs from EF5 only in the absence of fluorines on the side chain (see FIG. 2).

Another mouse, which had been immunized with a compound of the invention adducted to lysozyme was treated in a similar manner. Table 1 depicts the responses of the various clones to a large variety of proteins, each with versus without EF5 adducts. The initial screens of the clones were made based on a positive response to albumin-EF5, but a negative response to albumin alone. Of the sixteen clones examined, almost all possibilities of response were noted against the alternate antigens, but only two clones, #43 and #51, showed a strong differentially positive response against whole cell protein preparations from hypoxic cells incubated with EF5. Table 1 shows the importance of a wide variety of test antigens, the most important being whole cell protein digests, and that the techniques described can reliably produce mAb-producing hybridomas with high specificity to the desired antigens.

The dishes were then removed from the incubator, cooled to 0° C., and their medium replaced with drug-containing medium, first as a rinse (1 ml) which was simply aspirated and then as the actual medium used for the experiment (1 ml). Dishes were placed in leak-proof aluminum chambers which were connected to a manifold allowing them to be deoxygenated with a series of gas exchanges taking approximately thirty minutes. The confinement of cells to the central area of the dish, and the use of a small volume of medium allows very rapid equilibration of the gas and liquid phase to improve the control of oxygen concentration. Koch, 1984, supra. After deoxygenation, the chambers were incubated at 37° C. To prevent minor gradients of oxygen or potentially larger gradients of nutrients/metabolites, the chambers were also shaken gently (1 Hz, 2.5 cm stroke). To assay binding of radioactive nitroheterocyclics after incubation under defined experimental conditions, Koch, 1984, supra., the chambers were removed from the incubator and opened (allowing immediate reoxygenation), and the dishes were cooled on ice. The radioactive medium was removed. Two rinses with HEPES buffered Earle's balanced salt solution (EBSS) were followed by the addition of fresh medium and the dishes were incubated at 37° C. for 15 minutes. Another rinse in EBSS was followed by cell removal with 0.05% trypsin (40:1 dilution of SIGMA '40X') in calcium and magnesium free EBSS. An equal volume of serum-containing medium was added to stop the trypsin and a portion of the cell suspension was counted.

The cells were concentrated by centrifugation at 1000 rpm for ten minutes followed by resuspension in 200 µl of EBSS, on ice, and then the cells were disrupted by the addition of 100 microliter of 1M ice-cold trichloroacetic acid (TCA). The TCA precipitate was concentrated by centrifugation at 2500 rpm for 20 minutes. The TCA supernatant was saved and the pellet was dissolved in 0.2 ml of 1N NaOH, followed by neutralization with acetic acid. The clear TCA supernatant and the dissolved pellet were added with scintillation fluid to vials and counted in a Beckman liquid scintillation counter (LSC), resulting in a separation of acid soluble and acid precipitable counts. The above procedure results in background levels of incorporated radioactivity when radioactive sensitizers were incubated at low temperatures (4° C.) in hypoxia, or at 37° C. in air. Since the cell number, drug concentration and specific activity, and LSC efficiency were all known, the absolute incorporation of adducts could be calculated as picomoles per cell per hour of incubation at 37° C.

It can be seen in FIG. 1 that binding occurs to a much greater extent in hypoxic cells (circles) than cells at intermediate oxygen levels (~3 Torr—squares) and almost no binding is seen for cells containing a higher level of oxygen (15 Torr-triangles). In each case the solid symbols are for TCA precipitable adducts, and the open symbols are for TCA soluble adducts. The cells in this experiment were 9L rat glioma cells.

EXAMPLE 5
Testing the mAbs' Specificity Using ELISA Techniques

Figure 2:
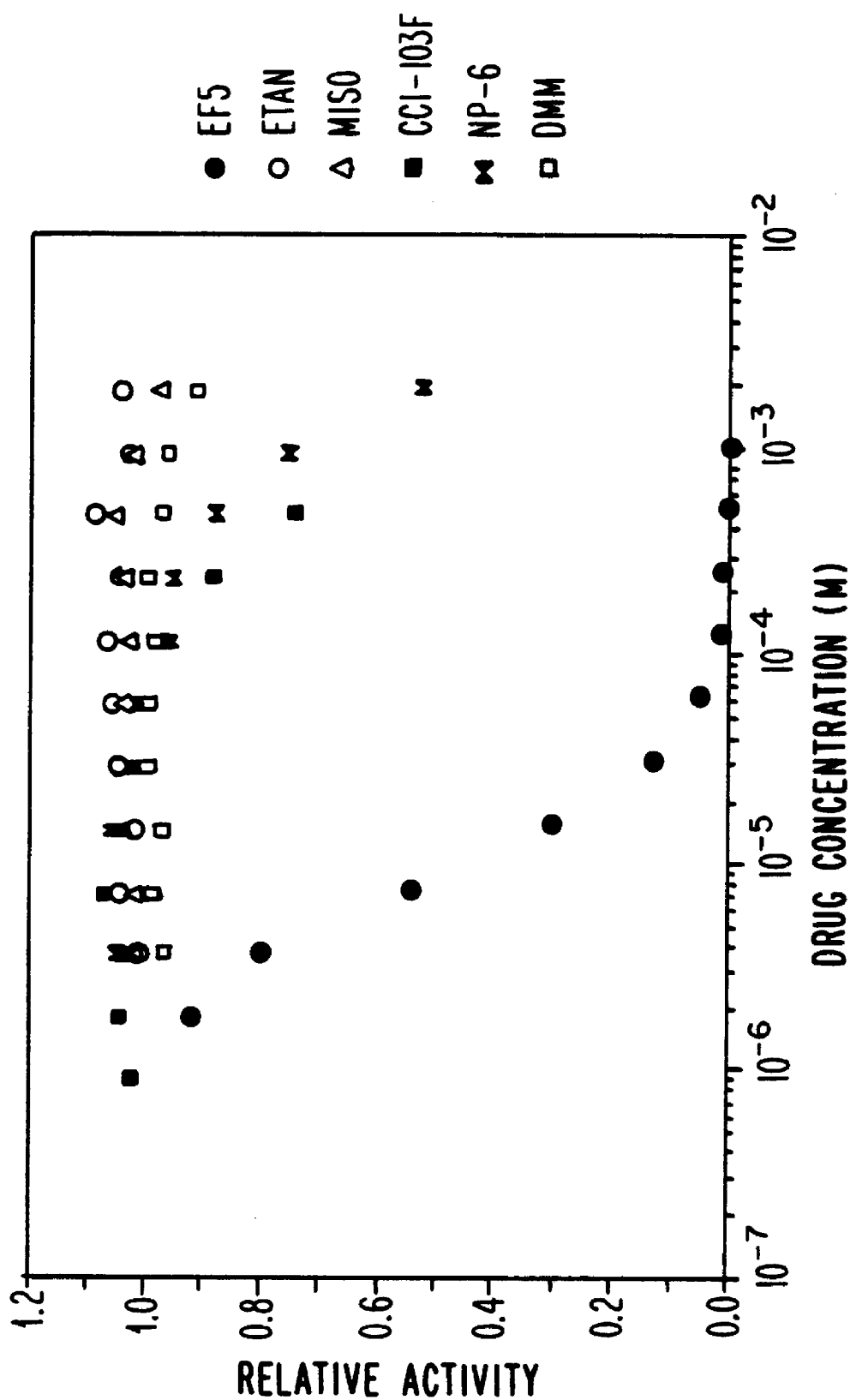
FIG. 2 is a graphical representation of the specificity of a mAb of the invention against several antigens. A mAb of the invention is at least 100 times more reactive toward EF5, than other, similar nitroaromatic drugs. The graph symbols are defined as follows: solid circles represent EF5; open circles represent etanidazole (ETAN); open triangles represent MISO; closed squares represent CCI-103F; crosses represent NP-6 (2,4-dinitro-1H-pyrrole-2-ethanol); and open squares are dimethylmisonidazole, 3-methoxy-1-[2-Nitro-4,5-dimethylimidazol-1-yl]-2-propanol (DMM).

FIG. 2 shows that the antibody designated ELK-2 recognizes only a compound of the invention, EF5, with a variety of other nitroaromatic compounds showing at least 100 fold less reactivity toward the antibody. The compounds are represented by the following symbols: solid circles represent EF5; open circles represent ETAN; the open triangles represent MISO; closed squares represent CCI-103F; crosses represent NP-6; and open squares are DMM.

Figure 3:
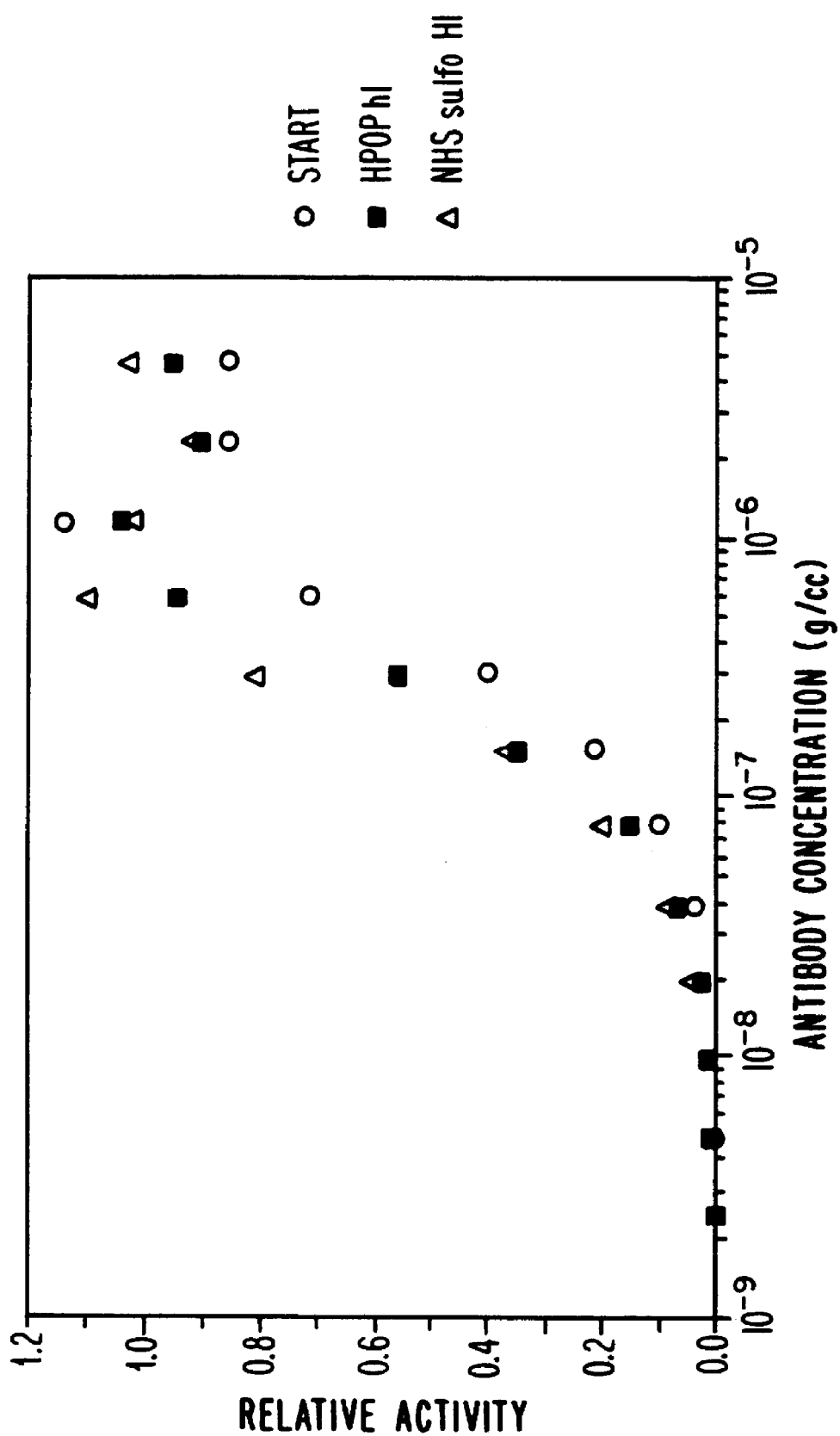
FIG. 3 is a graphical representation of the specificity of a mAb of the invention in several different forms, against a compound of the invention, EF5, adducted to BBI. The mAb was chemically modified to add a fluorescent moiety, amino methyl coumarin acetic acid (AMCA) using two different coupling chemistries. Fluorescent dyes may be conjugated onto mAbs of the invention without affecting the mAbs' activity. The graph symbols are defined as follows: open circles represent the monoclonal antibodies' specificity without the presence of the detection moiety, AMCA; closed triangles represent the coupling of the dye to an N-hydroxysulfocuccinimide group (NHSD sulfo Hi), which then reacts with primary amines of the protein of interest; closed squares represent similar methods where the reactive group is a pyridyldlthiopropionamide (HPDP hi), which reacts with free thiol groups on the protein of interest. The thiols were generated using mild radiochemical reduction methods (see Example 1) to reduce a small portion of the antibody's disulfide residues.

FIG. 3 demonstrates that addition of the AMCA fluorescent moiety to a monoclonal antibody of the invention, using two different coupling chemistries does not reduce its high specificity for its target antigen, the EF5-BBI conjugate. The open circles represent the monoclonal antibodies' specificity without the presence of the detection moiety. The AMCA molecules were added using standard protein modification kits available from Pierce, which involves the coupling of the dye to an N-hydroxysulfosuccinimide group (NHSD sulfo Hi-closed triangles), which then reacts with primary amines of the protein of interest, or similar methods where the reactive group is a pyridyldithiopropionamide (HPDP hi-closed squares), which reacts with free thiol groups on the protein of interest. The thiols were generated using mild radiochemical reduction methods (See Example 1) to reduce a small portion of the antibody's disulfide residues.

Figure 4:
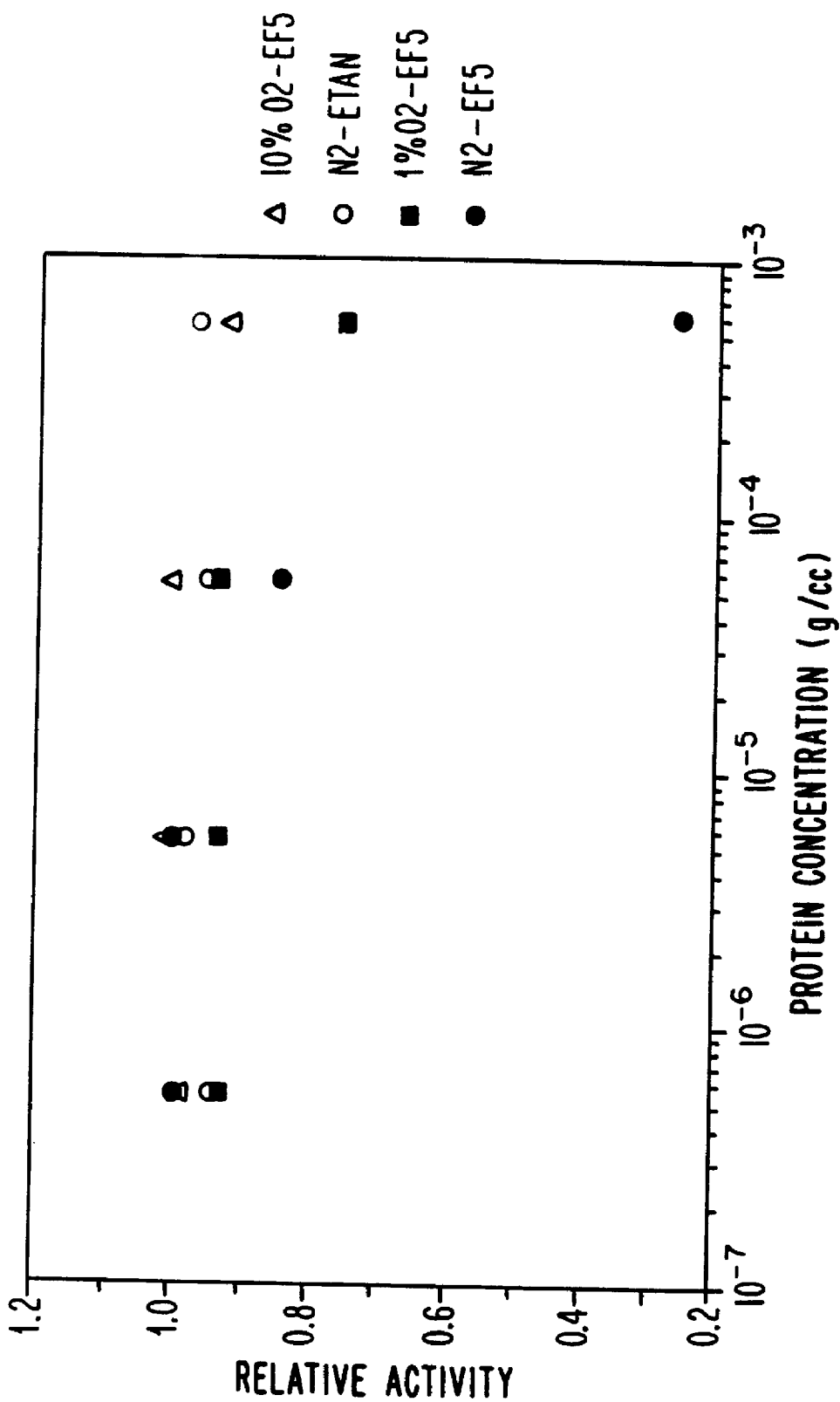
FIG. 4 depicts the binding, using ELISA based techniques, of a mAb of the invention to proteins derived from EMT-6 mouse cells. The cells were incubated with a compound of the invention at various levels of oxygenation, then the cells were harvested and whole-cell protein preparations were made. Proteins from aerobic cells did not react, proteins from cells incubated at moderately low oxygen levels, 15 Torr, were slightly reactive, while proteins from cells incubated at very low oxygen levels were highly reactive. The closed triangle represent the relative reactivity of EF5 with cells containing 10% oxygen; the open circles represent the relative reactivity of etanidazole in an anaerobic environment (nitrogen); the closed squares represent the relative activity of EF5 with cells containing 1% oxygen; and the closed circles represent the relative reactivity of EF5 in an anaerobic environment (nitrogen).

FIG. 4 represents an example of how a clinical assay could be performed. In this case, cells treated with EF5 under hypoxia were homogenized using standard protein extraction techniques. The resulting protein preparations were added to 96 well ELISA plates, as described above for Example 3, and analyzed using ELISA competition techniques. It can be seen that proteins from hypoxic cells were much more reactive than those from cells incubated at intermediate oxygen concentrations, and that proteins from aerobic cells were non-reactive. The closed triangle represent the relative reactivity of EF5 with cells containing 10% oxygen; the open circles represent the relative reactivity of etanidazole in an anaerobic environment (nitrogen); the closed squares represent the relative activity of EF5 with cells containing 1% oxygen; and the closed circles represent the relative reactivity of EF5 in an anaerobic environment (nitrogen).

Figure 5:
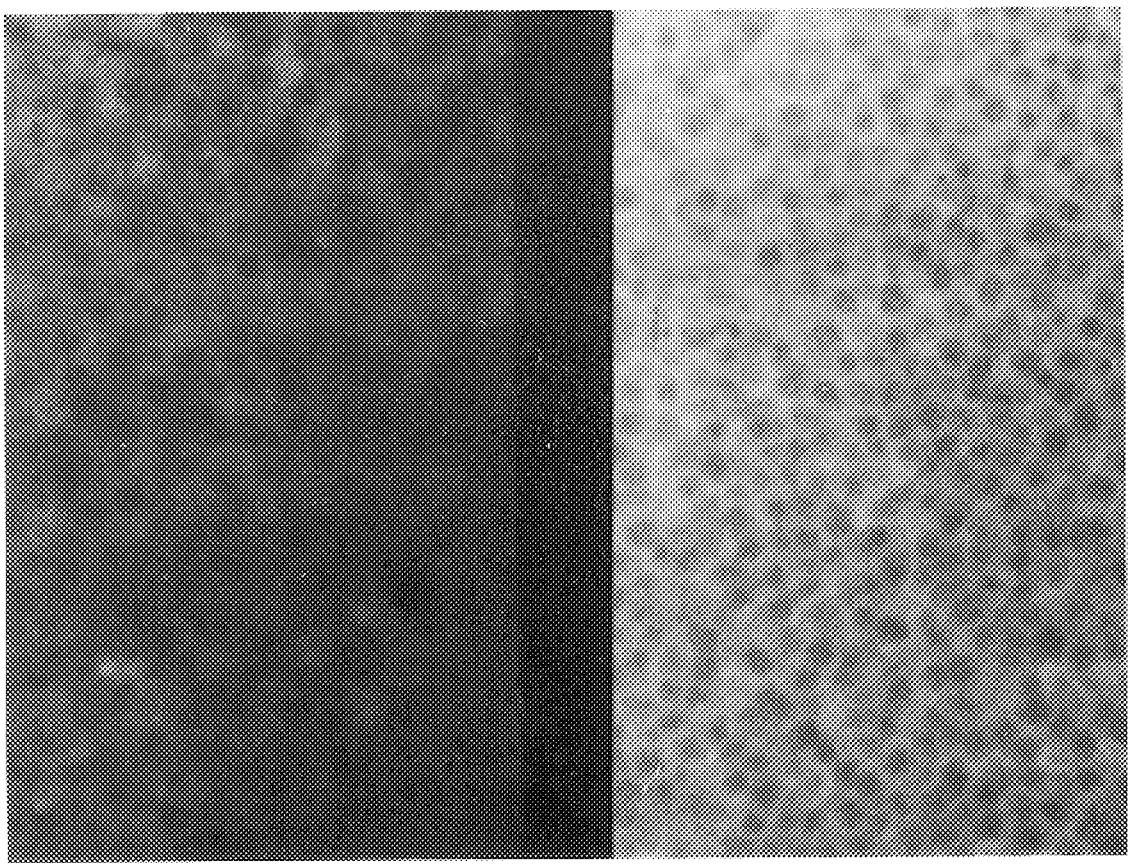
FIGS. 5–7 depict the immunohistochemical staining of various cells and tissues treated with a compound of the invention, then stained by mAbs of the invention.
Figure 6:
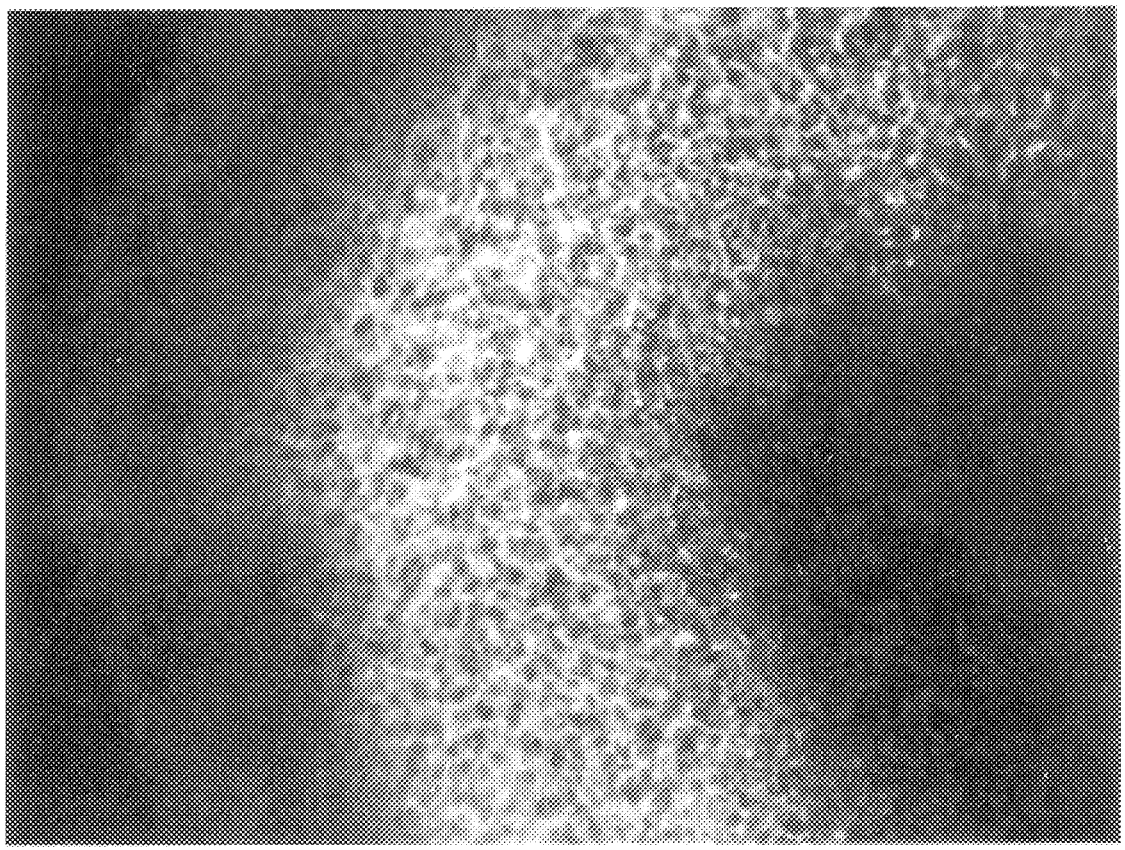
Figure 7:

EXAMPLE 6
Imaging Techniques (FIGS. 5–7)

Various cells and tissues, either caused or expected to contain hypoxic cells, were incubated with a compound of the invention, EF5, and then stained using a mAb of the invention, ELK-2. The binding of the antibody was visualized in one of two ways. First, utilizing a fluorescein-labelled second antibody (Jackson Laboratories) recognizing the isotype (mouse IgG1) of the ELK-2 antibody. Second, utilizing ELK-2 which had been made autofluorescent via the addition of AMCA as described above.

FIG. 5 compares the binding of antibody to 9L glioma cells treated with 0.5 mM EF5 in the presence of either air, represented by the dark region in the photomicrograph, versus nitrogen, represented by the light region on the photomicrograph. The exposures of drugs, antibodies, and photography were all identical in the two halves of the figure. Only the oxygen concentration during incubation was varied. The cells were allowed to attach to microscope slides, then they were air dried, and briefly exposed to a 0.1 solution of triton X-100, followed by rinsing to remove the detergent. The slides were treated overnight at 4° C. with ELK-2 antibody and rinsed for several minutes in PBS. They were then stained with fluorescein-labelled goat anti-mouse IgG1, rinsed to remove unbound second antibody, and observed using a fluorescent microscope.

FIG. 6 shows the results of a similar experiment where whole spheroids growing in spinner flasks were incubated with 0.5 mM EF5 for 4 hours. The spheroids were removed, washed, embedded in OCT compound and frozen on dry ice. Cryostat sections (10 micron thickness) were cut, placed on poly-L-lysine coated glass slides, and the sections fixed in 1% paraformaldehyde for 10 minutes. After rinsing, blocking antisera (2% normal goat serum) was added and incubated for 30 minutes at room temperature. The slides were treated with ELK-2 overnight at 4° C., and were then washed 3 times, then treated with a fluorescein-labelled second antibody as indicated above. The slides were then washed and observed with a fluorescent microscope. The photomicrograph shows that the outer rim of the spheroid is completely unstained, but that the staining intensity increases dramatically for cells in the spheroid interior which are expected to be hypoxic.

FIG. 7 represents another example, using an actual tumor bearing animal. A BALB/c mouse bearing an EMT6 tumor was injected intraperitoneally with 1.2 cc of 2 mM EF5. Forty-eight hours later, the mouse was sacrificed, the tumor removed, embedded in OCT compound and frozen on dry ice. Cryostat sections of about 20 microns thickness were cut, and the sections treated as above for the spheroid sections, except that only one antibody was used, namely the AMCA conjugated ELK-2 described above and in FIG. 4. The AMCA dye fluoresces in the blue, using UV excitation. The photomicrograph's bright areas are those expected to contain hypoxic cells. Various modifications of the invention in addition to those shown and described herein will be apparent to those skilled in the art from the foregoing description. Such modifications are also intended to fall within the scope of the appended claims.

EXAMPLE 7
Binding Affinity of Monoclonal Antibodies

The binding affinity of the monoclonal antibodies is of interest because higher affinity antibodies would allow the use of lower drug concentrations.

Figure 8:
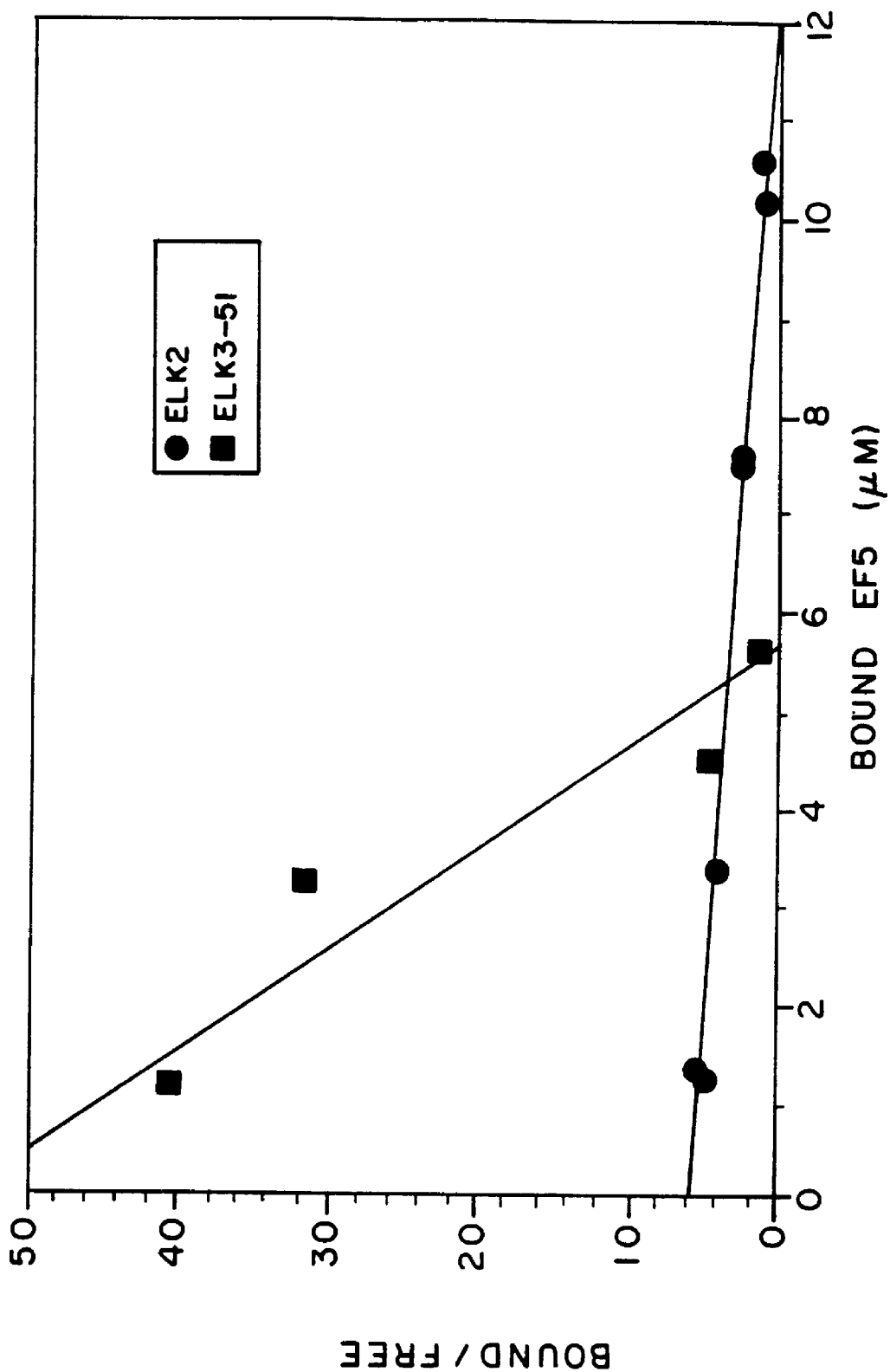
FIG. 8 depicts a comparison of the binding affinity of a monoclonal antibody (ELK-2) from one fusion (which used 2-(2-nitro-1H-imidazol-1-yl)-N-(2,2,3,3,3-pentafluoropropyl) acetamide (EF5)-BBI as antigen) with another monoclonal antibody (EKL3-51) from another fusion (which used EF5-lysozyme as antigen). A Skatchard analysis derives the binding affinity under conditions of equilibrium dialysis, wherein the concentrations of free drug versus bound drug (antibody-drug complex) are determined. The slope of the line represents the affinity constant: thus the affinity constant for ELK-2 is about $5 \times 10^5$, whereas the affinity constant for ELK3-51 is $5 \times 10^7$. This results indicates that ELK3-51 will be able to bind at roughly 20-fold lower 2-(2-nitro-1H-imidazol-1-yl)-N-(2,2,3,3,3-pentafluoropropyl) acetamide (EF5) concentrations than ELK-2.

The data depicted in FIG. 8 demonstrates the binding affinity of a monoclonal antibody (ELK-2) prepared from a fusion that used the antigen 2-(2-nitro-1H-imidazol-1-yl)-N-(2,2,3,3,3-pentafluoropropyl) acetamide (EF5—a pentafluorinated derivative of etanidazole) and the protein Bowan Birk inhibitor (BBI) and the binding affinity of another monoclonal antibody (EKL3-51) that was prepared from a fusion that used the 2-(2-nitro-1H-imidazol-1-yl)-N-(2,2,3,3,3-pentafluoropropyl) acetamide (EF5) and the protein lysozyme as antigen). A Skatchard analysis derived the binding affinity under conditions of equilibrium dialysis, wherein the concentrations of free drug versus bound drug (antibody-drug complex) are determined. The slope of the line represents the affinity constant: thus the affinity constant for ELK-2 is about $5 \times 10^5$, whereas the affinity constant for ELK3-51 is $5 \times 10^7$.

The affinity of the ELK3-51 antibody is sufficiently high that it can be used to image individual cells using the powerful technique of flow cytometry.

Figure 9:
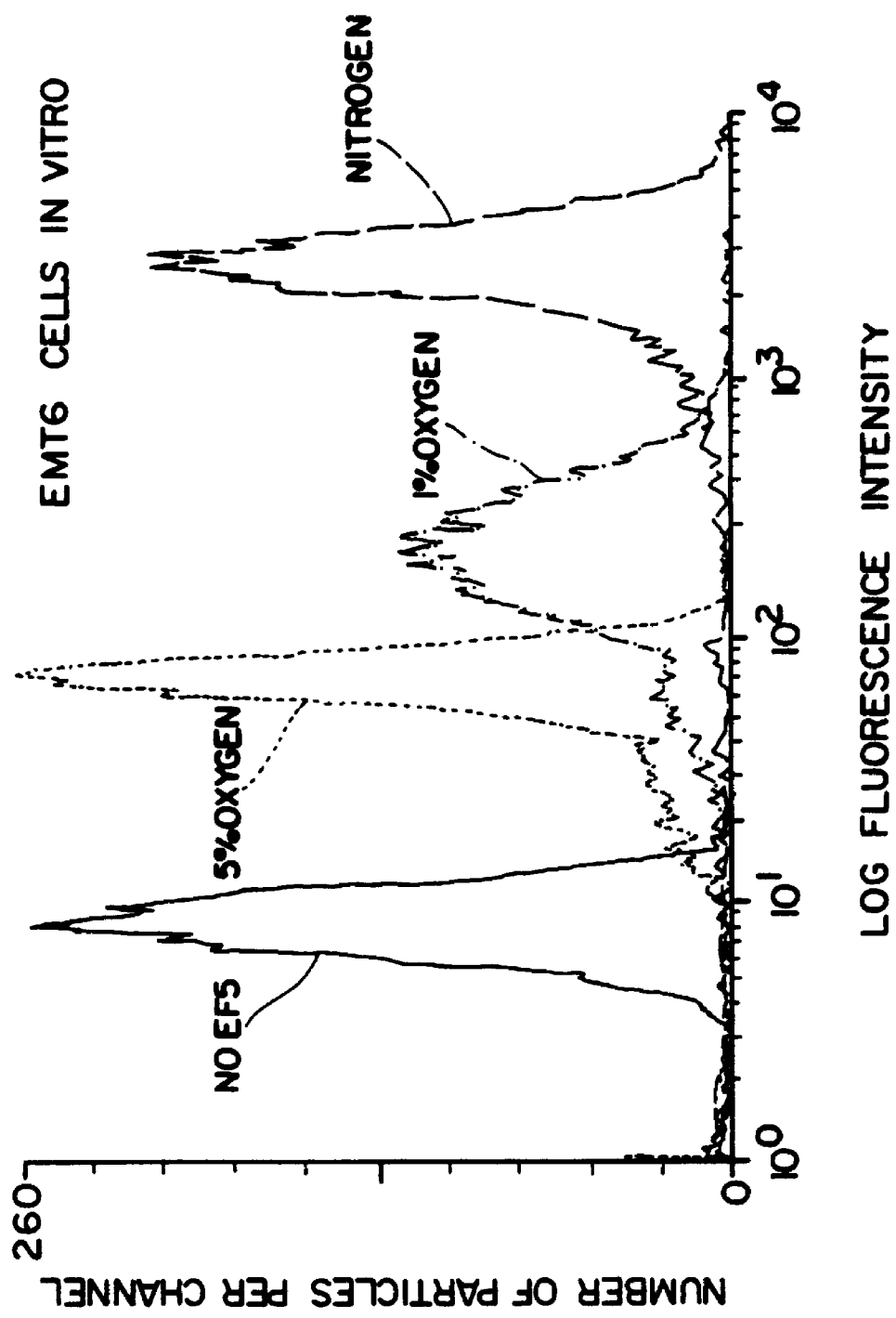
FIG. 9 depicts the results from flow-cytometry analysis. The four peaks illustrate the result of flow-cytometry analysis for EMT6 cells stained, using methods described herein, with ELK3-51 conjugated to the fluorochrome Cy3 (an emission fluorochrome contrasting with the emission AMCA originally described). Cells were incubated without drug (control—first peak, EF5 label) or with 100 $\mu$M EF5 for three hours in 5% oxygen (second peak, 5% oxygen label), 1% oxygen (third peak, 1% oxygen label) or nitrogen (<0.01% oxygen) (fourth peak, nitrogen label).

All aspects of the binding and antibody staining process are sufficiently stable to assess the hypoxia of individual cells. (FIG. 9).

EXAMPLE 8
Flow Cytometry Analysis for EMT6 Cells

EMT6 cells (mouse mammary carcinoma), were stained using methods described in the disclosure of this application, with ELK3-51 conjugated to the fluorochrome Cy3 (an emission fluorochrome contrasting with the emission AMCA originally described). Cells were incubated without drug (control—first peak, EF5 label) or with 100 $\mu$M 2-(2-nitro-1H-imidazol-1-yl)-N-(2,2,3,3,3-pentafluoropropyl) acetamide (EF5) for three hours in 5% oxygen (second peak, 5% oxygen label), 1 oxygen (third peak, 1% oxygen level) or nitrogen (<0.01% (fourth peak, nitrogen label). Flow-cytometery analysis was then carried out and the results are depicted in FIG. 9.

Figure 10:
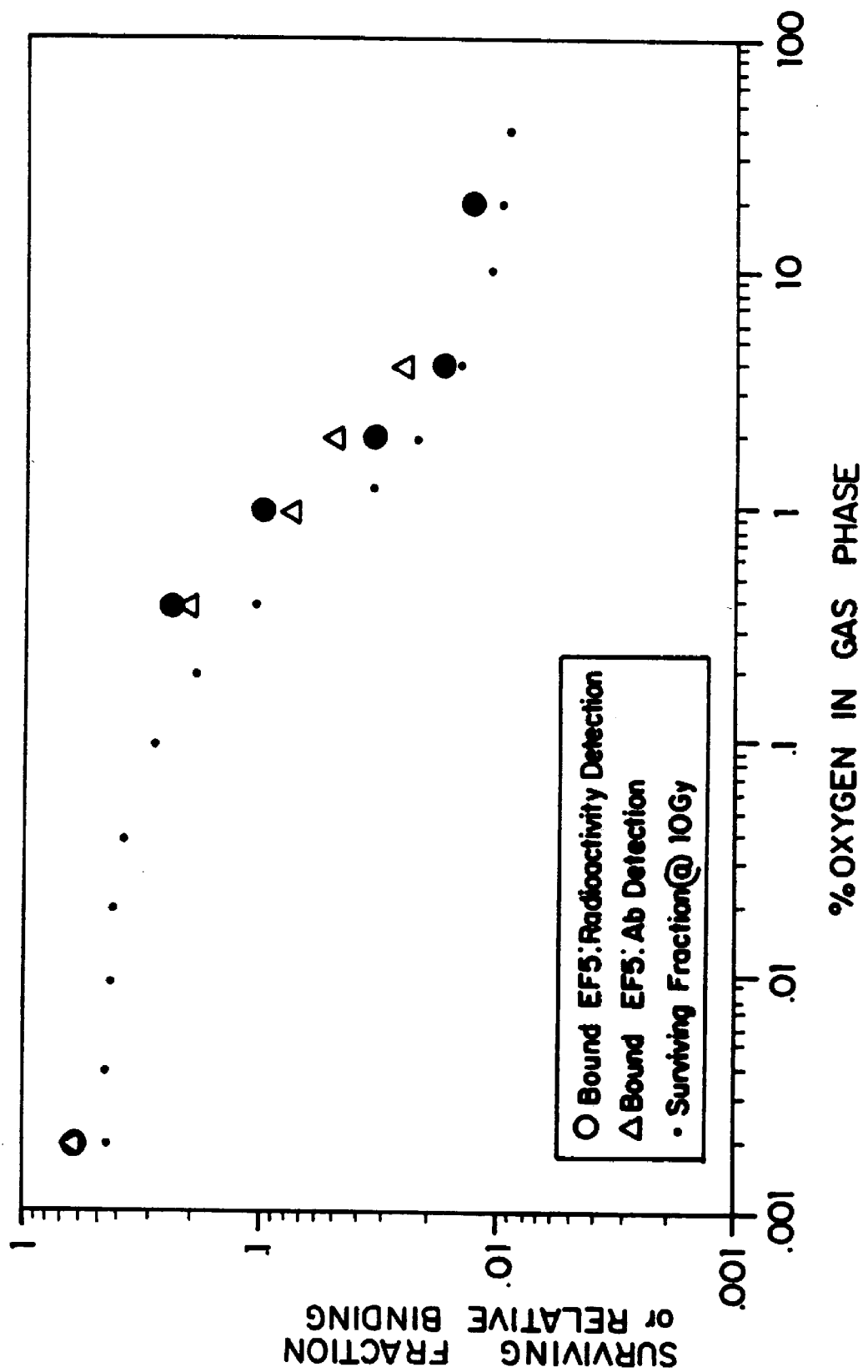
FIG. 10 depicts comparisons made between the oxygen dependence of (a) the survival of cells given 10 Gy (small dot) b) mean fluorescence intensity, derived from experiments such as those shown in FIG. 9 using flow cytometry (square) and (c) uptake of radioactive 2-(2-nitro-1H-imidazol-1-yl)-N-(2,2,3,3,3-pentafluoropropyl) acetamide (EF5) (large circle—e.g. see FIG. 1). The excellent correlation between the three assays shows that flow cytometric analysis of EF5-labelled cells can predict for cell survival.

The fluorescent signal unexpectedly provided a quantitative indication of the level of binding of one compound of the invention (a pentafluorinated derivative of etanidazole). (FIG. 10).

EXAMPLE 9
Oxygen Dependence

The oxygen dependence of various properties of cells were studied using the compounds and methods of the invention. Comparisons were made between the oxygen dependence of (a) the survival of cells given 10 Gy (small dot); b) mean fluorescence intensity, derived from experiments such as those shown in FIG. 9 using flow cytometry (square); and (c) uptake of a radioactive compound of the invention—a pentafluorinated derivative of etanidazole (large circle) (see FIG. 1). The excellent correlation between the three assays shows that flow cytometric analysis of 2-(2-nitro-1H-imidazol-1-yl)-N-(2,2,3,3,3-pentafluoropropyl) acetamide labelled cells can predict cell survival.

EXAMPLE 10
Flow Cytometry Analysis

Studies were done to test the predictive power of the flow cytometry analysis using a spheroid culture system. These studies showed that using the compounds and methods of the invention, changes in absolute radiation sensitivity can be predicted. (FIGS. 11 and 12).

The prediction discussed above in Example 9 was tested using the multicellular spheroid model, discussed above. Spheroids, grown in spinner flasks, are aggregates of several hundred thousand cells which develop hypoxic, radioresistant cells at their centers as a result of diffusion gradients of oxygen. These gradients are imposed by oxygen consumption of cells at the periphery of the spheroids, and have a genesis very much like those found in tumors. The hashmarks curve shows that flow cytometric analysis of cells from spheroids incubated with 100 $\mu$M EF5 in their "natural" growth state (i.e., the gas phase of the spinner flask contains air). The continuous-line curve illustrates the flow cytometric analysis of identically treated spheroids in an "oxygen supplemented" state (i.e. extras oxygen was added to the gas phase of the spinner flask). The flow cytometric analysis predicts that the "oxygenated supplemented" spheroids should be more radiation sensitive than those grown in their natural state. The aforementioned is depicted in FIG. 11.

Figure 11:
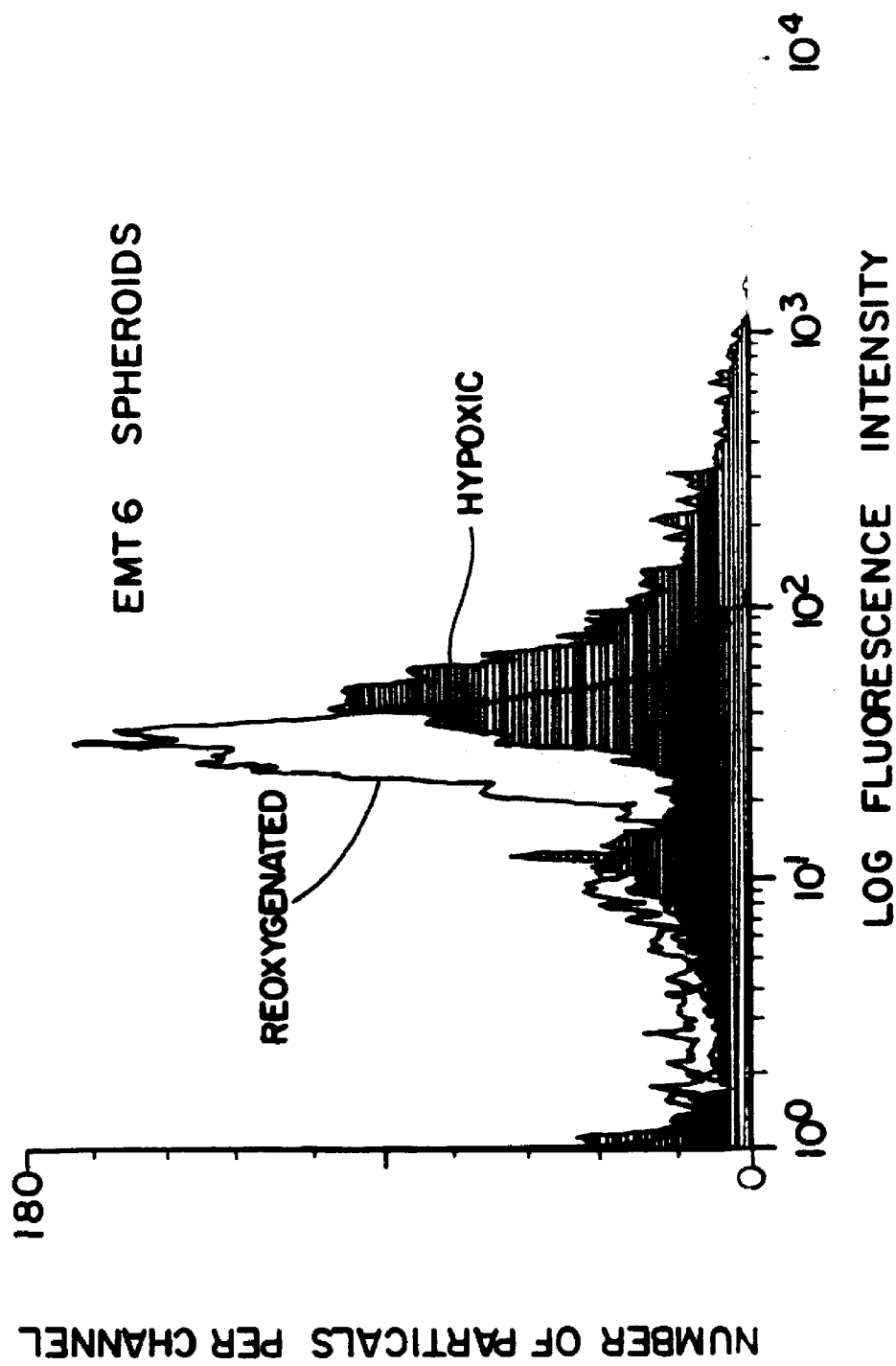
FIG. 11 is a further study of experiments described in FIG. 10.
Figure 12:
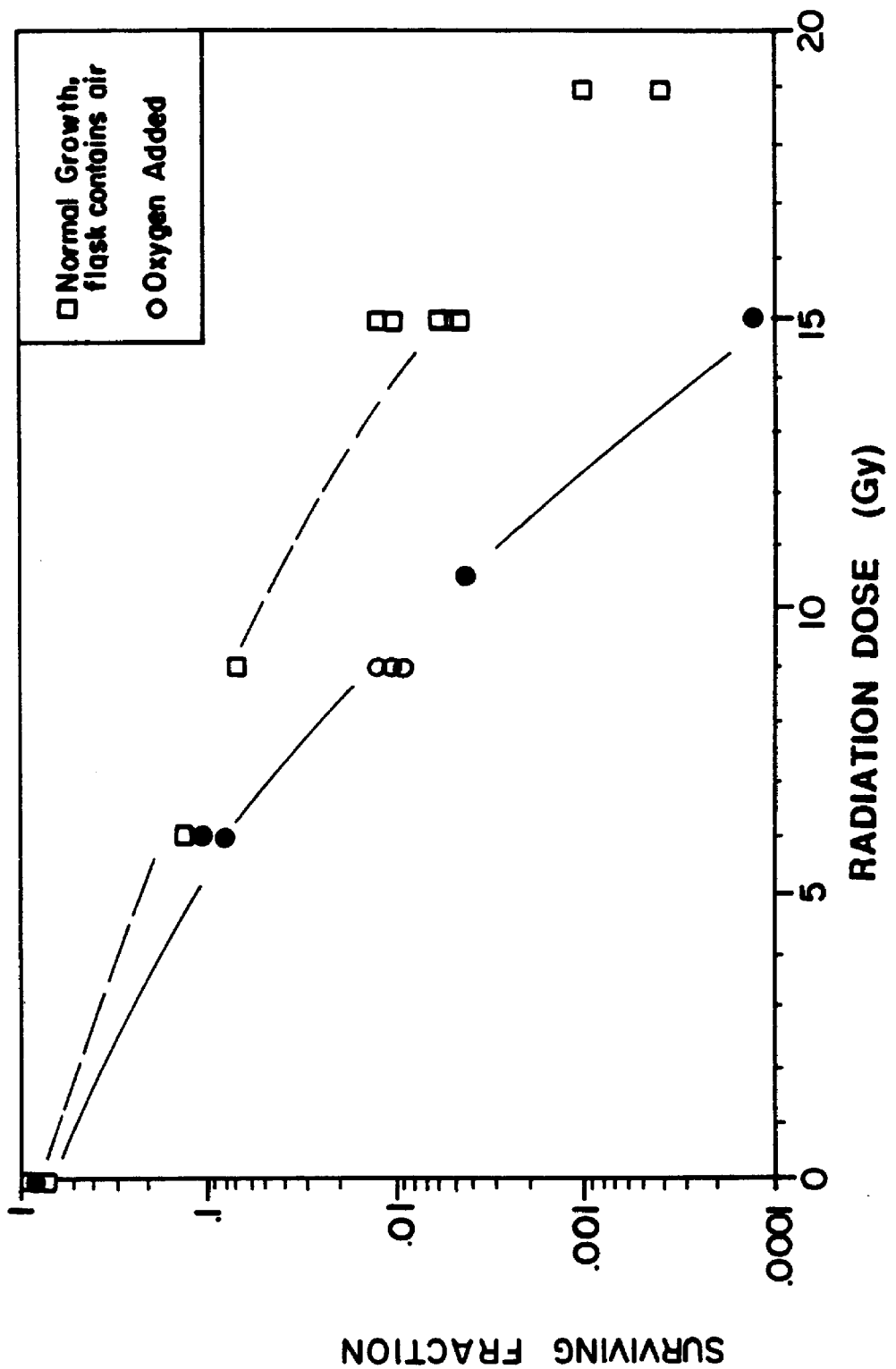
FIG. 12 depicts the survival curves for the cells from the spheroids of FIG. 11 which confirm that the addition of oxygen causes an increase in radiation sensitivity (cells within the spheroids are killed more efficiently by the same radiation dose).

Survival curves for the cells from the spheroids of FIG. 11 confirm that the addition of oxygen causes an increase in radiation sensitivity (cells within the spheroids are killed more efficiently by the same radiation dose).

Using the compounds and methods of the invention, the oxygen distribution in spheroids or more complex tumors and animal tissues can be analyzed after only one day, unlike method known in the art. This will allow, for the first time, the possibility of developing hypoxia assays in time to direct and affect tumor treatment.

EXAMPLE 11
Kinetics for the Compounds of the Invention

Figure 13:
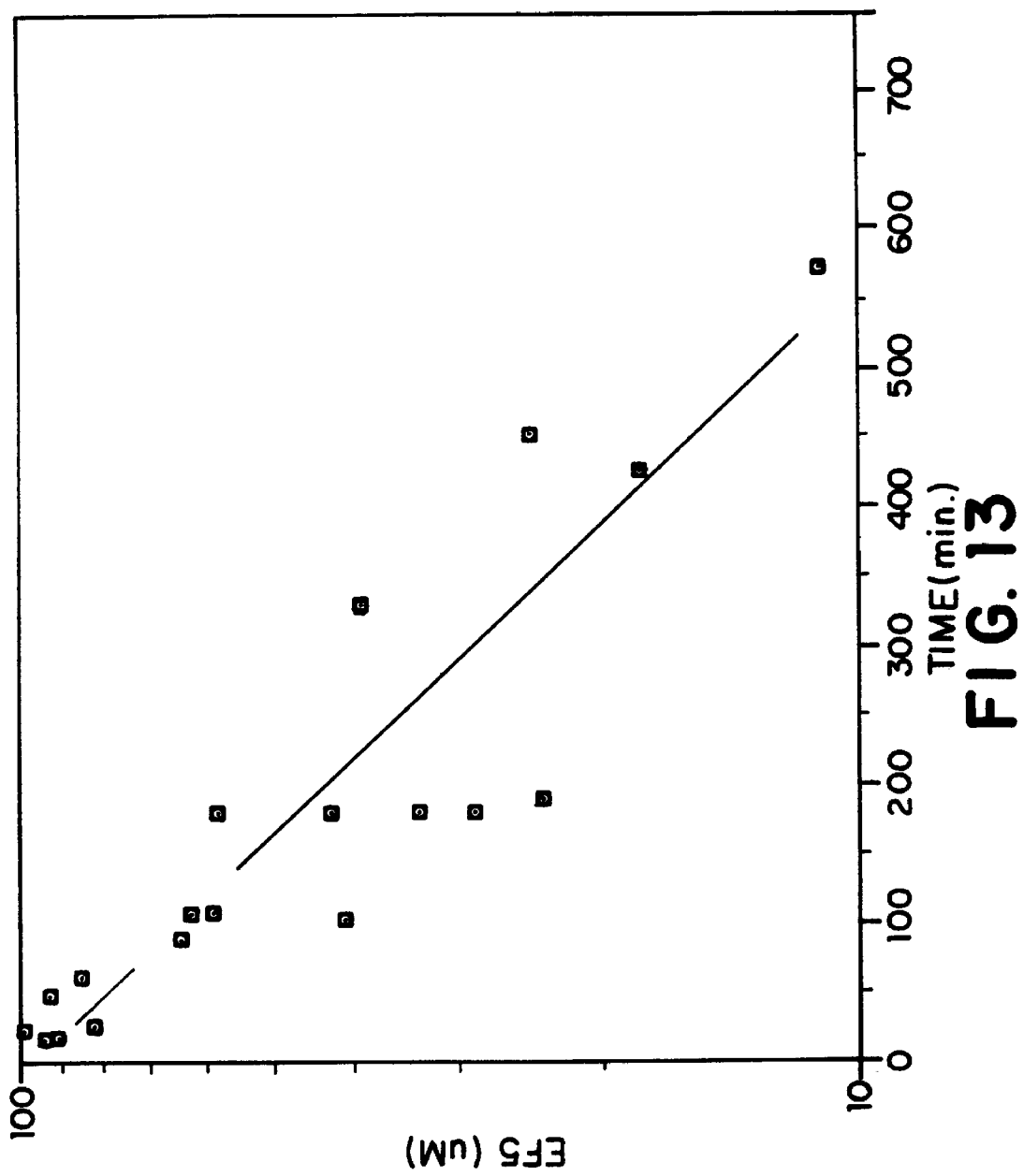
FIG. 13 depicts the serum concentration of 2-(2-nitro-1H-imidazol-1-yl)-N-(2,2,3,3,3-pentafluoropropyl) acetamide (EF5) in rats after intravenous administration. These data show a drug half-life (time for drug concentration to decrease by one-half) of about 150 minutes. Less extensive date in mice show a drug half-life of about 75 minutes. These results are very consistent wit other 2-nitroimidazoles of similar partition coefficient.

Studies have shown that with the compounds of the invention (i.e., a pentafluorinated derivative of etanidazole) there is no specific retention of drug, or variance from first-order kinetics that would be caused by non-specific tissue retention. (FIG. 13).

The serum concentration of a compound of the invention studied (a pentafluorinated derivative of etanidazole) in rats after intravenous administration shows a drug half-life (time for drug concentration to decrease by one-half) of about 150 minutes. Less extensive date in mice show a drug half-life of about 75 minutes. (FIG. 13).

EXAMPLE 12
Distribution of the Compounds of the Invention in Tissues

Figure 14A:
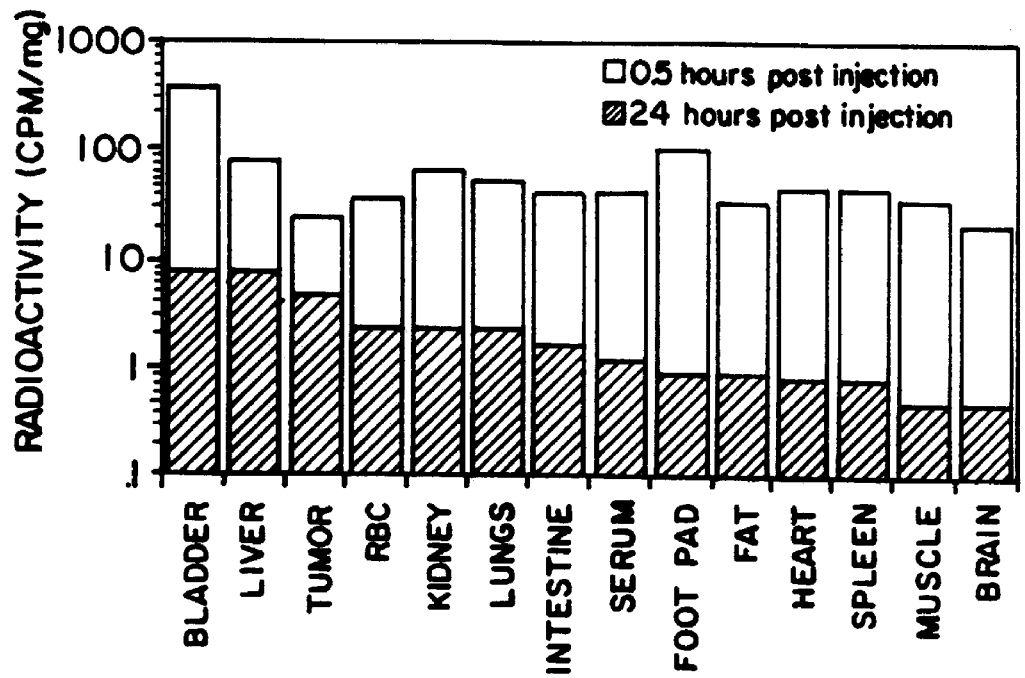
FIGS. 14A and 14B depict the tissue distribution of 2-(2-nitro-1H-imidazol-1-yl)-N-(2,2,3,3,3-pentafluoropropyl) acetamide (EF5) in mice. This was determined by digesting tissues 24 hours after intravenous administration of $^{14}$C-labelled EF5 (total concentration equivalent to 100 $\mu$M whole body). In contrast to misonidazole, where many tissues have similar amounts of bound drug to tumor, only liver has comparable levels of bound EF5 (bladder is an excretion route). Note particularly the achievement of equilibrium drug levels in brain tissue at short times after drug administration.
Figure 14B:
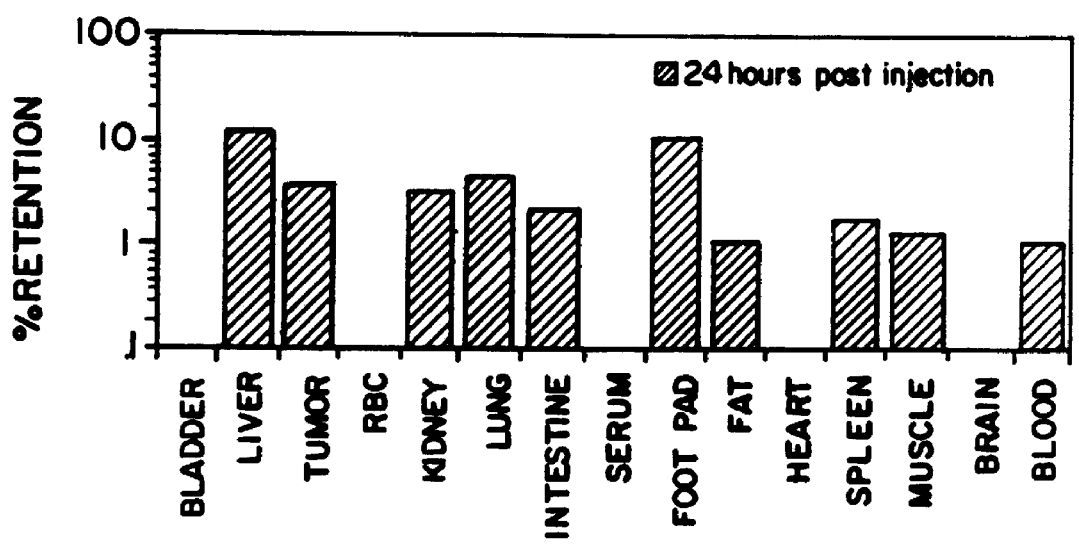

For a hypoxia detector, it is desirable to have a uniform drug distribution throughout the animal. 2-(2-nitro-1H-imidazol-1-yl)-N-(2,2,3,3,3-pentafluoropropyl) acetamide (EF5) because of its high lipid solubility, was found to have such a uniform distribution. (FIGS. 14a and 14b).

Tissue distribution of EF5 in mice was determined by digesting tissues 24 hours after intravenous administration of $^{14}$C-labelled EF5 (total concentration equivalent to 100 $\mu$M whole body). In contrast to misonidazole, where many tissues have similar amounts of bound drug to tumor, only liver has comparable levels of bound EF5 (bladder is an excretion route). Note particularly the achievement of equilibrium drug levels in brain tissue at short times after drug administration.

Studies have shown that the compounds of the invention, such as a pentafluorinated derivative of etanidazole (EF5), is a consistent hypoxia marker in vitro, and has similar advantages in vivo. (FIG. 14, panels A and B).

Fluorescent antibodies were used to stain sections from tumor (FIG. 15, panel A) versus liver (FIG. 15, panel B) in the same animal. The liver contains relatively uniform levels of intermediate oxygen (moderate fluorescence everywhere) whereas the tumor contains some regions of very low oxygen (bright fluorescence) but also a majority of regions with oxygen levels that are much higher (very low fluorescence). The example shown emphasizes the "bright" regions of the tumor, with the majority showing levels of binding more like the dark areas of the photograph. The 'average' drug uptake in various tissues cannot predict the drug distribution within the tissue—this can only be achieved using techniques involving the antibodies of the invention.

It has also been shown that the binding of a trifluorinated derivative of etanidazole EF3, 2-(2-nitro- 1H-imidazol-1-yl) -N-(3,3,3-trifluoropropyl) acetamide, (the trifluoro analogue of EF5. This derivative was administered via an intravenous injection at 100 pM whole-body to an EMT6-tumor-bearing mouse. Binding of the trifluorinated derivative was monitored by monoclonal antibodies to this drug. (FIG. 15, Panel C).

For all panels in FIG. 8; tissue sections are roughly 1000 μm×600 μm, 14 μm thickness.

Figure 15A:
FIGS. 15A–15C indicates the possibility that the present methods may not work well in liver, which should exist at oxygen levels significantly higher than the most hypoxic regions of tumors. Using the fluorescent antibodies to stain sections from tumor (15A) versus liver (15B) in the same animal explain this apparent discrepancy. The liver contains relatively uniform levels of intermediate oxygen (moderate fluorescence everywhere) whereas the tumor contains some regions of very low oxygen (bright fluorescence) but also a majority of regions with oxygen levels that are much higher (very low fluorescence). The example shown emphasizes the "bright" regions of the tumor, with the majority showing levels of binding more like the dark areas of the photograph. Thus, the 'average' drug uptake in various tissues cannot predict the drug distribution within the tissue—this can only be achieved using techniques involving the antibodies (or vastly more labor intensive techniques such as autoradiography)
Figure 15B:
Figure 15C:

Panel C of FIG. 15 shows recent results for a monoclonal antibody directed against EF3, 2-(2-nitro-1H-imidazol-1-yl) -N-(3,3,3-trifluoropropyl) acetamide, (the trifluoro analogue of EF5).

What is claimed is:

1. A method for preparing a monoclonal antibody comprising:
   a) introducing into a mammal a compound bound to a protein, the compound having the formula:

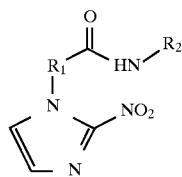

wherein $R_1$ is $CH_2$ and $R_2$ is an alkyl group having up to about 6 halogen atoms, wherein said alkyl group has the formula $CHXCX_2CY_3$ where X is halogen or hydrogen and Y is fluorine or bromine; and
   b) fusing immune cells of the mammal with mammalian myeloma cells forming a hybridoma that produces antibodies specific for the compound bound to the protein.

2. The method of claim 1 wherein the halogen atom is fluorine.

3. The method of claim 1 wherein $R_2$ is $CH_2CF_2CF_3$.

4. The method of claim 1 wherein $R_2$ is $CH_2CH_2CF_3$.

5. The method of claim 1 wherein the compound has at least five fluorine atoms.

6. The method of claim 1 wherein the protein is albumin, lysozyme, or Bowman Birk inhibitor.

7. The method of claim 1 wherein $R_2$ is $CH_2CF_2CF_3$, and the protein is Bowman Birk inhibitor.

8. The method of claim 1 wherein $R_2$ is $CH_2CF_2CF_3$, and the protein is lysozyme.

9. A monoclonal antibody specific for a compound, the compound's protein conjugate, the compound's reductive byproduct, or adduct formed between the compound and tissue protein, the compound having the formula:

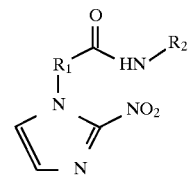

wherein $R_1$ is $CH_2$ and $R_2$ is an alkyl group having up to about 6 halogen atoms, wherein said alkyl group has the formula $CHXCX_2CY_3$ where X is halogen or hydrogen and Y is fluorine or bromine.

10. The monoclonal antibody of claim 9 wherein the halogen atom is fluorine.

11. The monoclonal antibody of claim 9 wherein $R_2$ is $CH_2CF_2CF_3$.

12. The monoclonal antibody of claim 9 wherein $R_2$ is $CH_2CH_2CF_3$.

13. The monoclonal antibody of claim 9 wherein the compound has at least five fluorine atoms.

14. A biological reagent kit comprising the monoclonal antibody of claim 9 bound to a detection moiety.

15. The kit of claim 14 wherein $R_2$ is $CH_2CF_2CF_3$, and the detection moiety is a fluorophore, biotin, or an enzyme.

* * * * *